United States Patent
Knittel et al.

(10) Patent No.: US 11,584,708 B2
(45) Date of Patent: Feb. 21, 2023

(54) SYNTHESIS OF (2S,3R,4R)-4,5-DIHYDROXYISOLEUCINE AND DERIVATIVES

(71) Applicant: Heidelberg Pharma Research GmbH, Ladenburg (DE)

(72) Inventors: Caroline Knittel, Berlin (DE); Mary-Ann Siegert, Berlin (DE); Roderich Süssmuth, Berlin (DE); Christoph Wink, Kelkheim (DE); Gerhard Jas, Berlin (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 0 days.

(21) Appl. No.: 17/042,323

(22) PCT Filed: Mar. 29, 2019

(86) PCT No.: PCT/EP2019/058034
§ 371 (c)(1),
(2) Date: Sep. 28, 2020

(87) PCT Pub. No.: WO2019/185877
PCT Pub. Date: Oct. 3, 2019

(65) Prior Publication Data
US 2021/0009507 A1    Jan. 14, 2021

(30) Foreign Application Priority Data

Mar. 29, 2018 (EP) .................................. 18165034

(51) Int. Cl.
| | | |
|---|---|---|
| *C07C 227/16* | (2006.01) | |
| *C07C 229/30* | (2006.01) | |
| *C07D 319/20* | (2006.01) | |
| *C07D 493/10* | (2006.01) | |
| *C07D 493/20* | (2006.01) | |
| *A61K 31/439* | (2006.01) | |
| *B01J 21/06* | (2006.01) | |
| *C07F 7/18* | (2006.01) | |

(52) U.S. Cl.
CPC .......... *C07C 227/16* (2013.01); *A61K 31/439* (2013.01); *B01J 21/063* (2013.01); *C07D 319/20* (2013.01); *C07D 493/10* (2013.01); *C07D 493/20* (2013.01); *C07F 7/1804* (2013.01); *C07C 229/30* (2013.01)

(58) Field of Classification Search
None
See application file for complete search history.

(56) References Cited

PUBLICATIONS

Bakke et al., "Action of L-Aminoacylase and L-Amino Acid Oxidase on 2-Amino-3-methylpent-4-enoic acid [Δ(4)-Dehydroisoleucine and alloisoleucine] Stereoisomers: An Alternative Route to a Stereochemically Pure Compound and the Application to the Synthesis of (R)-2-Methylbutan-1 -ol," *Synthesis*, 1999(9): 1671-1677 (1999).

Rabinowitz et al., "Design of Selective and Soluble Inhibitors of Tumor Necrosis Factor-α Converting Enzyme (TACE)," *J. Med. Chem.*, 44(24): 4252-4267 (2001).

Reuter, et al., "Stereoselective Synthesis of Proline-Derived Dipeptide Scaffolds (ProM-3 and ProM-7) Rigidified in a PPII HelixConformation," *Eur. J. Org. Chem.*, 2014(13): 2664-2667 and Supporting Information (2014).

Wang et al., "A Practical Synthesis of (2S,3R,4S)-4-Hydroxyisoleucine, A Potent Insulinotropic α-Amino Acid from Fenugreek," *Eur. J. Org. Chem.*, 2002(5): 834-839 (2002).

Zhao et al., "Synthesis of a Cytotoxic Amanitin for Biorthogonal Conjugation," *ChemBioChem*, 16(10): 1420-1425 and Supporting Information (2015).

European Patent Office, International Search Report in International Patent Application No. PCT/EP2019/058034 (dated Jun. 19, 2019).

European Patent Office, International Preliminary Report on Patentability in International Patent Application No. PCT/EP2019/058034 (dated Sep. 29, 2020).

*Primary Examiner* — Samantha L Shterengarts
(74) *Attorney, Agent, or Firm* — Leydig, Voit & Mayer, Ltd.

(57) ABSTRACT

The invention relates to a method for the preparation of a 4,5-dihydroxyisoleucine derivative comprising the steps of asymmetric Claisen rearrangement of a Z-aminocrotyl-glycin ester and subsequent kinetic resolution of the product diastereomer mix by acylase, and subsequent Sharpless dihydroxylation of the resulting 2-amino-3-methylpent-4-enoic acid derivative.

11 Claims, 4 Drawing Sheets

SYNTHESIS OF (2S,3R,4R)-4,5-DIHYDROXYISOLEUCINE AND DERIVATIVES

CROSS-REFERENCE TO RELATED APPLICATIONS

This patent application is the U.S. national phase of International Patent Application No. PCT/EP2019/058034, filed on Mar. 29, 2019, which claims the benefit of European Patent Application No. 18165034.2, filed on Mar. 29, 2018, which are incorporated by reference in their entireties herein.

Dihydroxyisoleucine is a non-proteinogenic, naturally occurring amino acid and constitutes a building block of the amanitin mushroom poison family of compounds. Amanitin conjugates are being investigated as candidates for targeted cancer therapy, which necessitates the development of efficient synthetic pathways for the unusual building blocks of these drugs.

EP2872479B1 discloses a stereoselective synthesis of dihydroxyisoleucine over 11 steps from aspartic acid, involving a complex protecting group strategy. The synthetic pathway involves reduction of the side-chain carboxylic acid to an alcohol and subsequent submission to Swern oxidation followed by a Wittig-type reaction to afford 2-aminopentanoic acid, which is submitted to a Sharpless dihydroxylation. The overall yield is calculated to be only 3%, leading to unfavourable economies when applying this synthesis at industrial scale.

Furthermore, the synthesis of EP2872479B1 uses acetylation to prevent the side-chain hydroxyl groups from lactone formation upon deprotection of the carboxyl terminus. This may lead to racemization under strongly basic conditions.

Based on the above-mentioned state of the art, the objective of the present invention is to provide means and methods to provide an efficient synthesis for the title compound. This objective is attained by the claims of the present specification.

Terms and Definitions

The term "protecting group" in the context of the present specification relates to a moiety covalently attached to a functional group (particularly the carboxylic acid moiety, the amino moiety or the hydroxyl moiety of the molecules discussed herein) that can be selectively attached to the functional group and selectively removed without affecting the integrity or chiral orientation of the carbon backbone of the molecule the protecting group is attached to, nor cleaving particular other protecting groups attached to other protecting groups attached to the molecule.

A comprehensive review of modern protecting group chemistry, particularly as it pertains to the compounds disclosed herein, is available in Peter G. M. Wuts, Greene's Protective Groups in Organic Synthesis, 5th Edition, Wiley 2014.

U.S. Pat. No. 6,693,178 B2—"Protecting groups useful in the synthesis of polysaccharides, natural products, and combinatorial libraries" and US 20160024143 A1—"Deprotection method" are incorporated herein by reference.

Standard convention of organic chemistry, by which a non-designated position in a formula is deemed to be a saturated carbon, is followed herein.

The term $C_1$-$C_4$ alkyl in the context of the present invention signifies a saturated linear or branched hydrocarbon having 1, 2, 3 or 4 carbon atoms, wherein in certain embodiments one carbon-carbon bond may be unsaturated and one $CH_2$ moiety may be exchanged for oxygen (ether bridge) or nitrogen (NH, or NR with R being methyl, ethyl, or propyl; amino bridge). Non-limiting examples for a $C_1$-$C_4$ alkyl are methyl, ethyl, propyl, prop-2-enyl, n-butyl, 2-methylpropyl, tert-butyl, but-3-enyl, prop-2-inyl and but-3-inyl. In certain embodiments, a $C_1$-$C_4$ alkyl is a methyl, ethyl, propyl or butyl moiety.

A $C_1$-$C_6$ alkyl in the context of the present invention signifies a saturated linear or branched hydrocarbon having 1, 2, 3, 4, 5 or 6 carbon atoms, wherein one carbon-carbon bond may be unsaturated and one $CH_2$ moiety may be exchanged for oxygen (ether bridge) or nitrogen (NH, or NR with R being methyl, ethyl, or propyl; amino bridge). Non-limiting examples for a $C_1$-$C_6$ alkyl include the examples given for $C_1$-$C_4$ alkyl above, and additionally 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl, pent-4-inyl, 3-methyl-2-pentyl, and 4-methyl-2-pentyl. In certain embodiments, a $C_5$ alkyl is a pentyl moiety and a $C_6$ alkyl is a hexyl or cyclohexyl moiety.

The term unsubstituted $C_n$ alkyl when used herein in the narrowest sense relates to the moiety —$C_nH_{2n}$— if used as a bridge between moieties of the molecule, or —$C_nH_{2n+1}$ if used in the context of a terminal moiety.

Where used in the context of chemical formulae, the following abbreviations may be used: Me is methyl $CH_3$, Et is ethyl —$CH_2CH_3$, Prop is propyl —$(CH_2)_2CH_3$ (n-propyl, n-pr) or —$CH(CH_3)_2$ (iso-propyl, i-pr), but is butyl —$C_4H_9$, —$(CH_2)_3CH_3$, —$CHCH_3CH_2CH_3$, —$CH_2CH(CH_3)_2$ or —$C(CH_3)_3$.

ASPECTS OF THE INVENTION

A first aspect of the invention relates to a method for the preparation of (2S,3S)-2-aminopent-4-enoic acid (30),

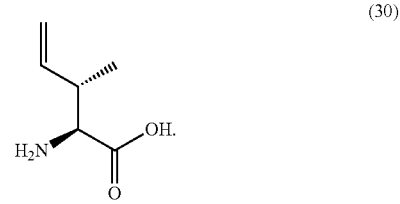

(30)

The process comprises a Claisen rearrangement step on a Z-crotyl-glycin ester derivative (200),

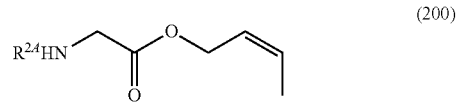

(200)

under conditions favourable to Claisen rearrangement of (200) in the presence of a chiral ligand (comprising a C=C double bond) to yield 2-aminopent-4-enoic acid derivative (300),

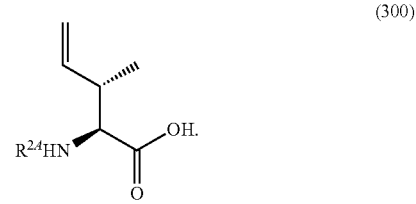

(300)

$R^{2A}$ is an amino protecting group stable under conditions favourable to Claisen rearrangement. In certain embodiments, $R^{2A}$ in general is an acyl group. In certain embodiments, $R^{2A}$ is tert-butoxycarbonyl. In certain embodiments, $R^{2A}$ is $CH_xF_{3-x}(CH_yF_{2-y})_nCO$— wherein n is 0 or 1, x is selected from 0, 1, 2 and 3 and y is selected from 0, 1 and 2.

In certain embodiments, $R^{2A}$ is $CF_3CO$—. In certain embodiments, $R^{2A}$ is $CHF_2CO$—. In certain embodiments, $R^{2A}$ is $CH_2FCO$—. In certain embodiments, $R^{2A}$ is acetyl.

In certain embodiments, $R^{2A}$ is $CF_3CF_2CO$—. In certain embodiments, $R^{2A}$ is $CH_3CF_2CO$—.

In certain particular embodiments, $R^{2A}$ is trifluoroacetyl.

In certain embodiments, the chiral ligand is selected from ephedrin, valinol, cinchonidine, cinchonine and quinidine.

In certain embodiments, the diastereoselectivity of the Claisen rearrangement step is 90:10, in particular, 93:7, more particularly 94:6.

The transition state of the Claisen rearrangement with quinidine as the chiral ligand is depicted by the following structure. The skilled person will be able to choose other chiral ligands suitable for carrying out the invention.

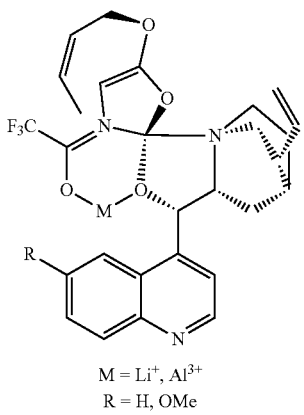

$M = Li^+, Al^{3+}$
$R = H, OMe$

In certain particular embodiments, the chiral ligand is quinidine.

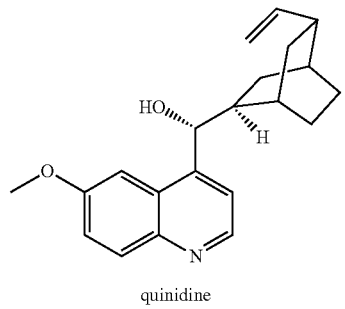 [SMILES: C=CC1CC2CCC1C[C@@H]2[C@@H](O)c1ccnc2ccc(OC)cc12]

quinidine

In certain embodiments, the chiral ligand, particularly the quinidine, is present in 2 to 3 molar equivalents in relation to compound 200.

In certain embodiments, the Claisen rearrangement step proceeds in the presence of a strong non-nucleophilic base soluble in (non)-polar organic solvents, particularly a lithium alkylamide or lithium silylalkylamide, more particularly a base selected from LDA (lithium diisopropylamide), LiHMDS (lithium bis(trimethylsilyl)amide) and LiTMP (lithium tetramethylpiperidine). The corresponding potassium bases may be used alternatively.

Certain particular embodiments of the Claisen rearrangement step are shown in Scheme 1:

Scheme 1 Claisen rearrangement of glycine cis-crotyl esters 21 and 29.

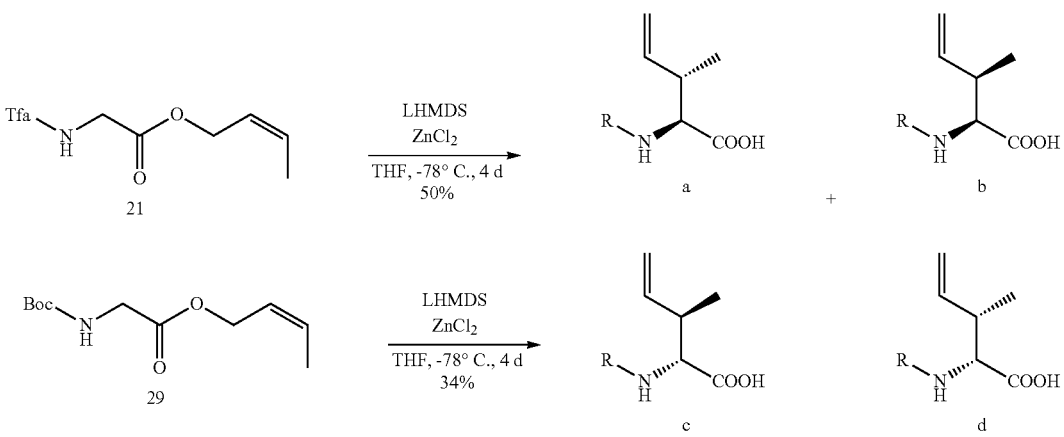

31a-d: R = Tfa
39a-d: R = Boc

The ester enolate Claisen rearrangement of the glycine cis-crotyl esters 21 and 29 can be performed following the protocol of Kazmaier et al. (*Angew. Chem. Int. Ed. Engl.* 1994, 33, 998-999). If $R^{2.4}$ is selected to be Tfa (trifluoroacetyl), lithium diisopropylamide (LDA) to some degree cleaves Tfa from the amine group of the glycine ester 21. Therefore, in their examples, the inventors chose lithium bis(trimethylsilyl)amide (LHMDS). The skilled artisan is capable of identifying numerous alternatives of the strong base without inventive activity.

In the hands of the inventors, the [3,3]-sigmatropic rearrangement of the Cbz-protected cis-crotyl ester did not yield the expected product, whereas the Boc-protected cis-crotyl ester (29) afforded relatively low yields (34%) with various byproducts. The best yield (50%) could be achieved with the Tfa-protected cis-crotyl ester (21) with lesser by-products. The reaction time in the absence of chiral ligand was surprisingly long (4 d) and did not coincide with the literature, where it was reported that the rearrangement takes place while the reaction mixture is warming up to room temperature in a range of −30° C. and −20° C. Here the reaction was only complete after the fourth day when the reaction mixture had already been stirred at room temperature for three days.

Methylation of the Tfa-protected rearrangement product (31) at the C-terminus and subsequent chiral GC-MS revealed that, according to expectations, the reaction had not proceeded in a stereospecific way. The chiral GC-MS chromatogram shows that both (R,R) and (S,S) enantiomers were formed to the same extent (FIG. 4). Thus, there is no enantiomeric excess. The diastereoselectivity was calculated to be 93:7. The inventors assume, without wanting to be limited by theory, that formation of the anti-products (2S,3S and 2R,3R) is favoured during the [3,3]-sigmatropic rearrangement, because of the chair-like transition state of the chelate-bridged ester enolate.

Scheme 2. Transition state of the chelate-bridged ester enolate

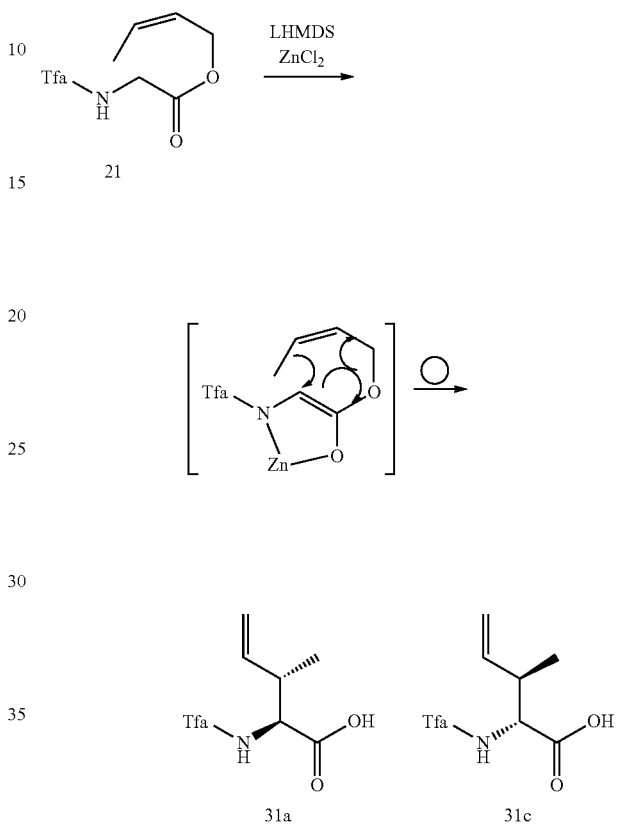

Introduction of a chiral ligand into the reaction mix however led to a very favorable enantiomeric excess of the desired (2S,3S)-enantiomer product in the case of quinidine.

Scheme 3 Asymmetric Claisen rearrangement

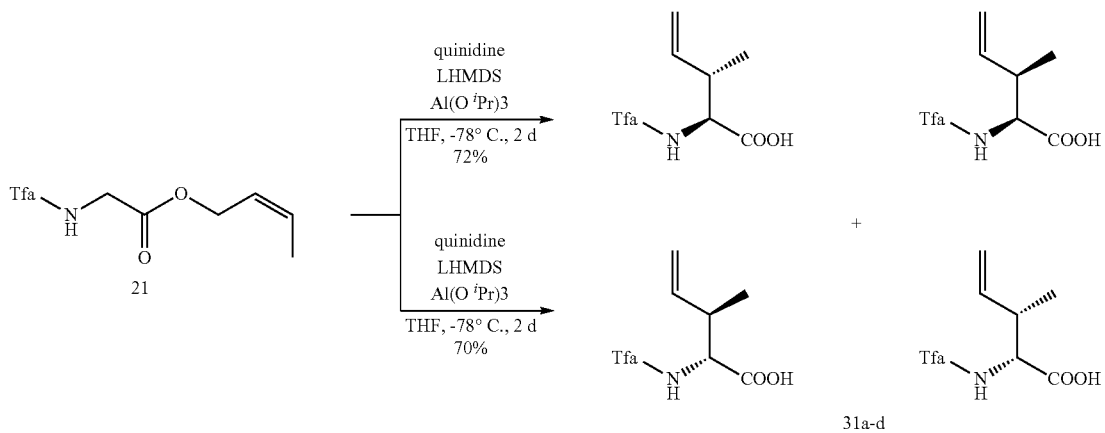

The Claisen rearrangements resulted in better yields and shorter reaction times in presence of quinidine or quinine than without the ligands. The yield was 72% using quinidine and 70% using quinine. The reaction was complete after only two days instead of four. Subsequent methylester formation and submission of the products to chiral GC-MS confirmed that the formation of the anti-products is favored.

The chiral GC-MS chromatogram of the asymmetric Claisen rearrangement product using quinine as ligand (FIG. 1) shows that the (R,R)-enantiomer was formed with an enantiomeric excess (ee) of 76%. The diastereoselectivity (ds) was calculated to be 83:17. Quinine is therefore not a suitable ligand for the purpose of the invention, as the desired (S,S)-enantiomer is only formed to an extent of 10%.

The GC-MS chromatogram of the asymmetric Claisen rearrangement product with quinidine as ligand (FIG. 2) shows that the (S,S)-enantiomer was formed with an enantiomeric excess (ee) of 87%. The diastereoselectivity (ds) was calculated to be 94:6. Quinidine is therefore a particularly suitable ligand for the purpose of this invention, but in general it can also be replaced by cinchonine in certain embodiments.

The following table resumes and compares the achieved yields, ee and ds values of the asymmetric Claisen rearrangements:

TABLE 1

Yields, enantioselectivities (ee) and diastereoselectivity (ds) of the asymmetric Claisen rearrangement with quinidine and quinine as ligands.

| ligand | yield [%] | ds | ee [%] | conf |
|---|---|---|---|---|
| quinidine | 72 | 94:6 | 87 | (S,S) |
| quinine | 70 | 83:3 | 76 | (R,R) |

The process according to the invention further comprises an enzymatic resolution step, wherein 2-aminopent-4-enoic amide derivative (310) is converted to yield (2S,3S)-2-aminopent-4-enoic acid (30).

Scheme 4 Enzymatic resolution step

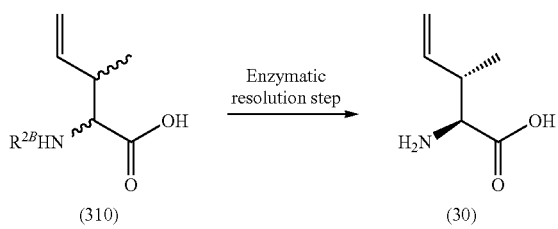

In certain embodiments, the enzymatic resolution step is effected by an acylase, particularly by acylase I from *Aspergillus* sp., more particularly acylase I from *Aspergillus melleus*.

In certain embodiments, $R^{2B}$ is trifluoroacetyl ($CF_3COO$).
In certain embodiments, $R^{2B}$ is $CF_3CF_2COO$.
In certain embodiments, $R^{2A}$ is the same as $R^{2B}$ and the enzymatic resolution step is performed directly after the Claisen rearrangement step.

In one exemplary reaction sequence, the Tfa-protected Claisen rearrangement product (31a-d) was directly submitted to enzymatic kinetic resolution. The trifluoroacetyl group was surprisingly determined to be a suitable substrate for the acylase enzyme. The reaction of the TFA protected substrate takes place at about half the reaction rate as the cleavage of the acetyl protected one, while omitting the strongly basic TFA-deprotection and acetylation steps.

Scheme 5 Enzymatic kinetic resolution without prior TFA-deprotection and acetylation of 31a-d affording the fully deprotected (2S,3S) and (2S,3R)-4,5 didehydro-isoleucine.

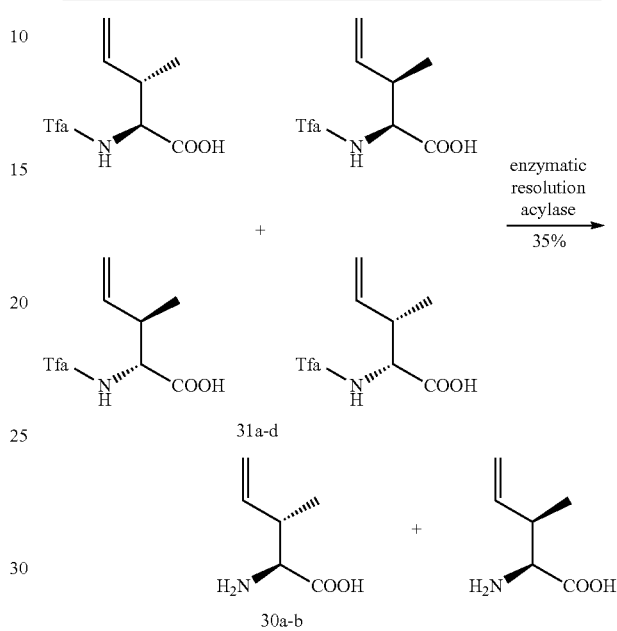

The product of the resolution (30a-b) was submitted to GC-MS, after trifluoroacetylation of the N-terminus and methylation of the C-terminus. The chiral GC-MS chromatogram (FIG. 3) shows that no racemization occurred by omitting the TFA-deprotection and acetylation steps prior to the enzymatic resolution. The diastereoselectivity was calculated to be 94:6 and the enantiomeric excess 92%. Even though the acylase specifically targets the L-configured amino acid, a small amount of the D-configured amino acid gets deprotected over the time. This residual racemization can be avoided by choosing shorter reaction times.

Yields of the enzymatic kinetic resolution products were calculated after purification using a strongly acidic ion cation exchange resin (for example: Dowex® 50WX8 hydrogen form). As cleavage from this resin is performed under basic conditions, minor racemization occurred. This means that strongly basic conditions need to be avoided during this synthesis pathway as the molecule tends to racemize easily upon treatment with strong bases after the Claisen rearrangement step. The crude product evolving from the following enzymatic resolution reactions with acylase was therefore submitted to the next reaction step without further purification.

Acylase resolution of the enriched diastereomeric product mixture yielded by the asymmetric Claisen step appears to be an important, and difficult to replace, feature of the method of the present invention, as non-enzymatic dynamic kinetic resolution of the Claisen rearrangement product using a Ni(II)-salt and a chiral proline based ligand under strongly acidic conditions resulted in the racemization towards the undesired (R,R)-enantiomer.

Scheme 6 Synthesis of (2S,3S)-2-aminopent-4-enoic acid (30) by use of Claisen rearrangement and enzymatic resolution (p = amino protecting group)

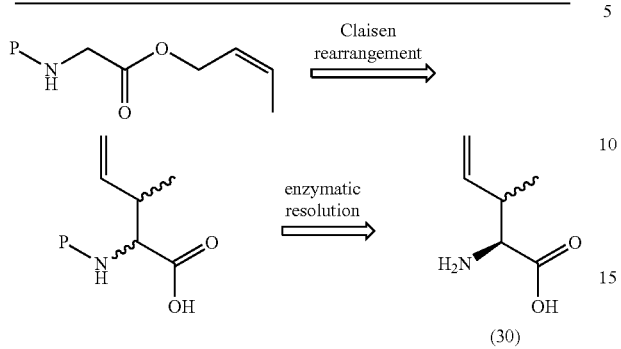

A second aspect of the invention relates to a method for the preparation of a 2-amino-3-methylpent-4-enoic acid derivative selected from

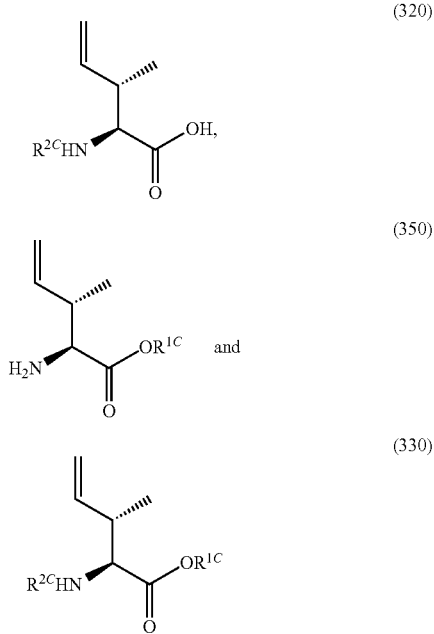

departing from the crotylglycinester (200).

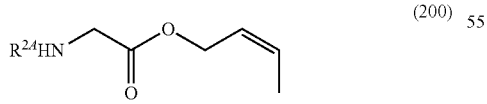

The method comprises the method according to the first aspect of the invention described above and comprises further:

a) a step of introducing an amino group protecting moiety $R^{2C}$ to the (2S,3S)-2-aminopent-4-enoic acid (30) or to a derivative of (30), thereby modifying the amino moiety by a protecting group moiety to yield (320) or —if step b) was performed before this step a), to yield (330), and/or b) a step of introducing a carboxylic acid group protecting moiety $R^{1C}$ to the (2S,3S)-2-aminopent-4-enoic acid (30) or the derivative (320) obtained in step a), thereby modifying the carboxylic acid moiety modified by a protecting group moiety to yield (350) or (330).

A third aspect of the invention relates to a method for the preparation of a 4,5-dihydroxyisoleucine derivative (400) departing from the crotylglycinester (200).

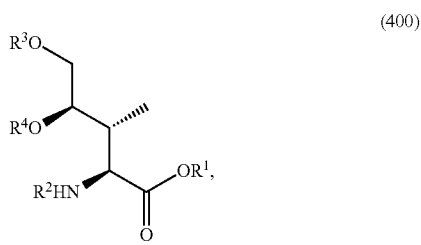

wherein
$R^1$ is H or a carboxylic acid moiety protecting group,
$R^2$ is H or an amino moiety protecting group and
$R^3$ and $R^4$ are independently from another selected from H and a hydroxyl moiety protecting group, or both $R^3$ and $R^4$ are one single vicinal diol protecting group moiety.

The method according to this aspect of the invention comprises the method according to the first and second aspect of the invention and further comprises a Sharpless dihydroxylation step, wherein 2-amino-3-methylpent-4-enoic acid derivative (330)

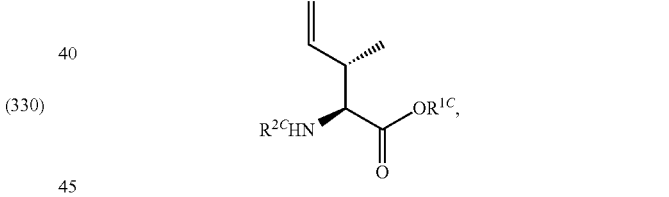

is reacted in the presence of Os(VIII) complexed by a chiral ligand to the 2-amino-3-methyl-4,5-dihydroxypentanoic acid derivative (430)

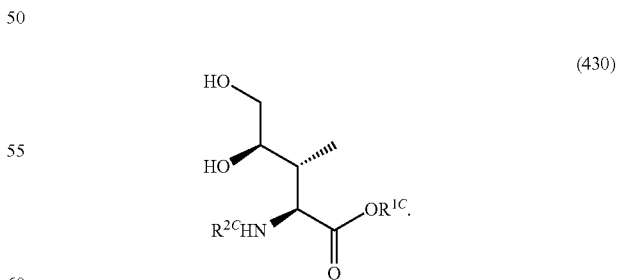

In certain embodiments, the chiral ligand is hydroquinidine 1,4-phthalazinediyl diether [(DHQD)$_2$-PHAL CAS Number 140853-10-7 (mix beta)].

In certain embodiments, the Sharpless dihydroxylation reaction is performed in the presence of (K$_2$OsO$_2$(OH)$_4$ and one of K$_3$Fe(CN)$_6$ and N-methylmorpholine N-oxide.

In certain embodiments, $R^{1C}$ is tert-butyl (—C(CH$_3$)$_3$), cyclopropylmethyl or dicyclopropylmethyl. These carboxyl protecting groups has proven to offer advantages when employed during the Sharpless dihydroxylation step.

In certain embodiments, $R^{2C}$ is fluorenylmethyloxycarbonyl (Fmoc). This enables the product of the Sharpless reaction to be used without further modification with respect to the amino function in standard solid phase peptide synthesis reaction chemistry.

Sharpless dihydroxylation of Fmoc-protected aminopentanoic esters having different carboxylic acid protecting groups such as triisopropylsilyl, heptyl or trichloroethyl, to differing degrees led to the formation of a very stable lactone (99). Edagawa et al. reported in 2009 that ring opening of this type of lactone results in the epimerization of the C$_\alpha$-atom, which is why the ring opening of 99 was not attempted.

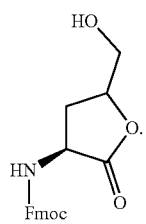

99

Sharpless dihydroxylation of the Fmoc-protected tert-butyl ester 36 particularly favoured the formation of the C- and N-terminally protected 4,5-dihydroxynorvaline. Without wishing to be bound by theory, the inventors assume that this is due to the strong steric hindrance and high stability of the tBu-ester.

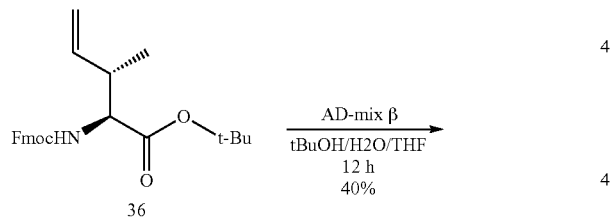

In one exemplary reaction sequence, enzymatic resolution product (30) was furnished with Fmoc and tBu at the N- and C-terminus. The following asymmetric Sharpless dihydroxylation resulted in the formation of both, lactone (111) and (2S,3R,4R)-4,5-dihydroxyisoleucine (46). Conversion of the terminal alkene 36 was not complete after 12 h. This might be the reason why the formation of the lactone took place. Prevention of the lactone formation might be achieved by using a higher amount of catalyst while keeping the reaction time to a maximum of 12 h. Cooling the reaction mixture might also help to prevent the elimination reaction of the tert-butyl group from the C-terminus.

Scheme 7 Asymmetric Sharpless dihydroxylation of 4,5-didehydroisoleucine (36) resulting in the formation of 4,5-dihydroxyisoleucine (46) and highly stable lactone (111) after 24 h.

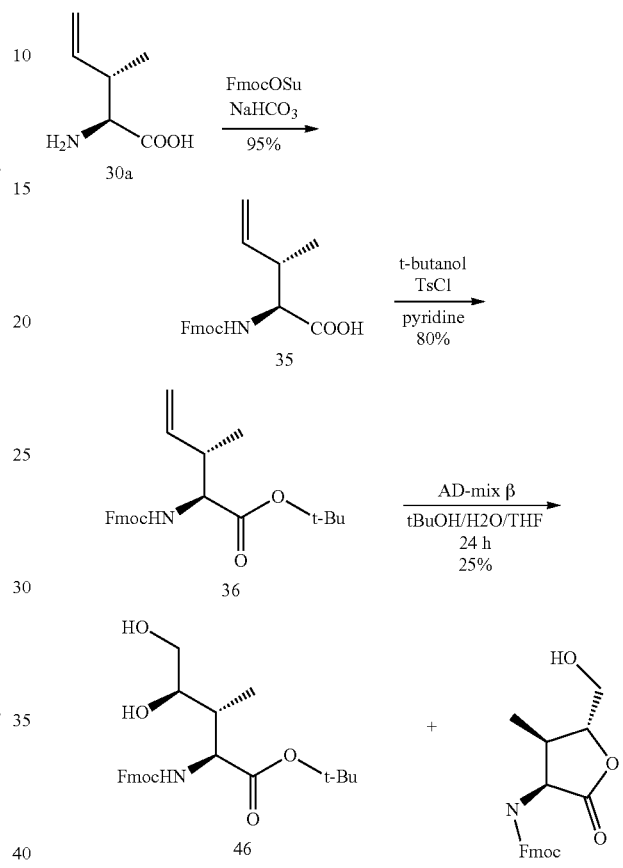

FmocOSu: N-(9-Fluorenylmethoxycarbonyloxy)succinimide

Scheme 8 Reaction scheme of an embodiment showing the synthesis of 4,5-dihydroxyisoleucine combining the first, second and third aspect of the invention

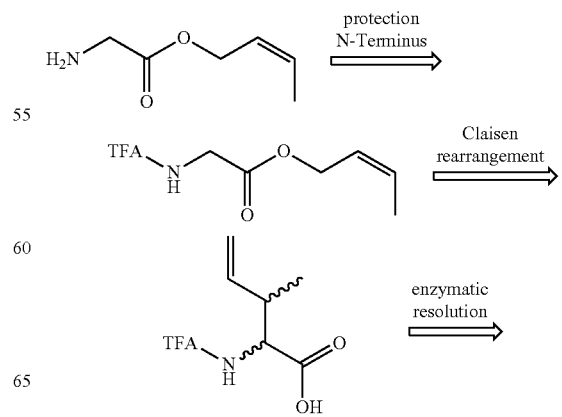

-continued

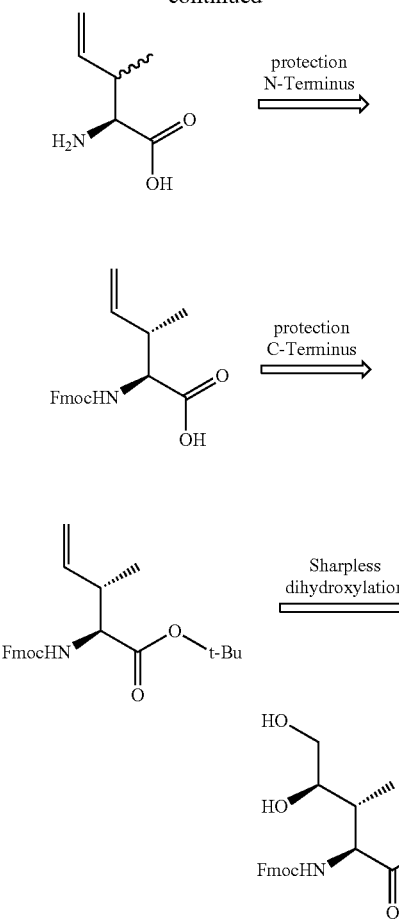

A fourth aspect of the invention relates to a method for the preparation of a (2S,3R,4R)-4,5-dihydroxyisoleucine derivative 400,

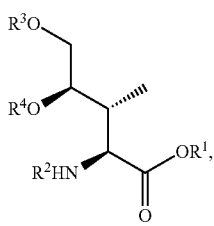

(400)

wherein
R¹ is H or a carboxylic acid moiety protecting group,
R² is H or an amino moiety protecting group and
R³ and R⁴ are independently from another selected from and a hydroxyl moiety protecting group, or both R³ and R⁴ are one single vicinal diol protecting group moiety.

The method comprises the method according to any one of aspects one or two of the invention and further comprises a diastereoselective epoxidation step as it is represented by the Sharpless approach or a related epoxidation according to Shi et al., *Org. Lett.*, 2001, 3, 1929-1931. Therein 2-amino-3-methylpent-4-enoic acid derivative (330)

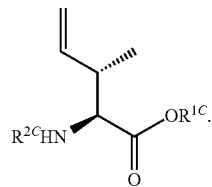

(330)

is reacted in the presence of a chiral ligand and a catalyst comprising titanium isopropoxide to a (2S,3S,4R)-2-amino-3-methyl-4,5-epoxy-pentanoic acid derivative (360),

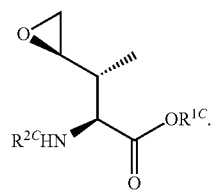

(360)

Next, the epoxide ring of (2S,3S,4R)-2-amino-3-methyl-4,5-epoxy-pentanoic acid derivative (360) is either opened by
i.) an enzymatic conversion catalysed by e.g. a fungal epoxide hydrolase (as described in Trend in Biotechnology, 22 (3), 123-139, 2004) into 2-amino-3-methyl-4,5-dihydroxypentanoic acid derivative (430),

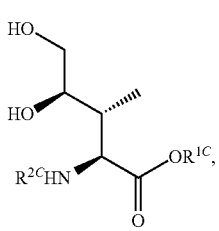

(430)

or
ii.) a reaction in the presence of a reducing agent to a 2-amino-3-methyl-5-hydroxypentanoic acid derivative (410). A non-limiting example for a reducing agent suitable for this step is sodium bis(2-methoxyethoxy)aluminium hydride ("RedAl").

Alternatively, the olefin (330) can be transformed by a hydroboration reaction to (410) according to Vedejs et al., *J. Am. Chem. Soc.* 2005, 127, 5566-5567.

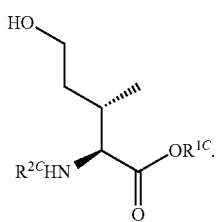

(410)

The epoxide ring of the (2S,3S,4R)-2-amino-3-methyl-4,5-epoxy-pentanoic acid derivative (360) is converted by an enzymatic reaction by an epoxide hydrolase in an enantioselective way, yielding 2-amino-3-methyl-4,5-dihydroxypentanoic acid derivative (430).

(430)

In certain embodiments, the use of Sharpless epoxidation and enzymatic enantioselective dihydroxylation as an alternative to Sharpless dihydroxylation is used in combination with the first aspect of the invention as shown in Scheme 9.

Scheme 9 Reaction scheme of an embodiment showing the synthesis of 4,5-dihydroxyisoleucine combining the first, second and fourth aspect of the invention.

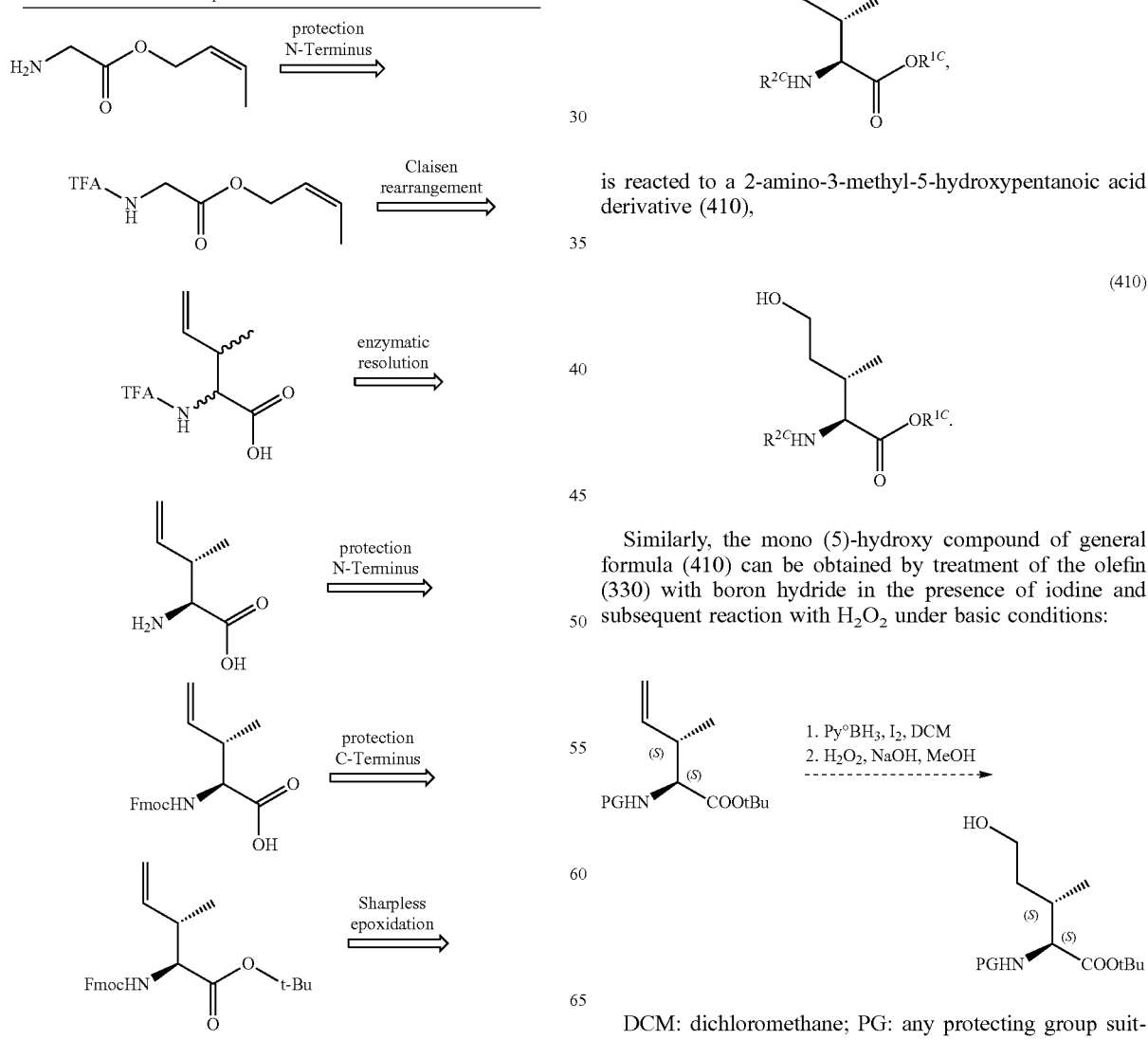

In certain embodiments, the product of the Sharpless epoxidation step (2S,3S,4R)-2-amino-3-methyl-4,5-epoxypentanoic acid derivative (360), (360)

is reacted to a 2-amino-3-methyl-5-hydroxypentanoic acid derivative (410), (410)

Similarly, the mono (5)-hydroxy compound of general formula (410) can be obtained by treatment of the olefin (330) with boron hydride in the presence of iodine and subsequent reaction with $H_2O_2$ under basic conditions:

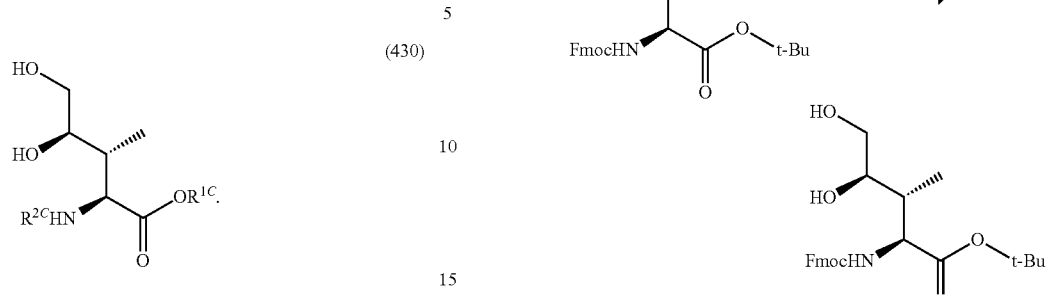

DCM: dichloromethane; PG: any protecting group suitable to the conditions employed; t-Bu: tert-butyl.

In certain embodiments, the product of the Sharpless epoxidation step (2S,3S,4R)-2-amino-3-methyl-4,5-epoxypentanoic acid derivative (360),

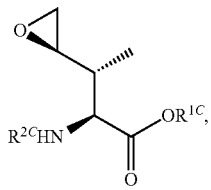
(360)

is reacted to a 2-amino-3-methyl-4-hydroxypentanoic acid derivative (440) by terminal, reductive opening of the epoxide (360) using reductive agents like complex hydrides.

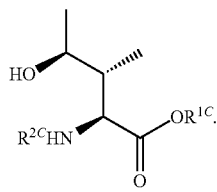
(440)

The skilled person understands that while the critical feature of the present invention relies in the sequence enabling early generation and maintenance of the (2R,3S) diastereomer, a number of final derivatives of the target molecule (2S,3R,4R)-4,5-dihydroxyisoleucine (40) are facilitated thereby. These are variations of the general structure (400):

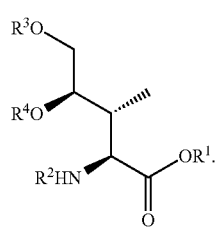
(400)

In certain embodiments, $R^1$ is H. In certain embodiments, $R^1$ is H and $R^2$ is Fmoc. In certain embodiments, $R^1$ is H, $R^2$ is Fmoc and $R^3$ and $R^4$ are a silyl-based hydroxyl protecting group. In certain embodiments, $R^1$ is H, $R^2$ is Fmoc and $R^3$ and $R^4$ are trialkylsilyl. In certain embodiments, $R^1$ is H, $R^2$ is Fmoc and $R^3$ and $R^4$ are trimethylsilyl. In certain embodiments, $R^1$ is H, $R^2$ is Fmoc and $R^3$ and $R^4$ together are a benzyl or a substituted phenylmethyl (e.g. p-methoxy benzylidene), a dialkyl-substituted silyl group or a tetrasubstituted siloxane moiety.

In certain embodiments, $R^1$ is tert-butyl (—C(CH$_3$)$_3$), cyclopropylmethyl or dicyclopropylmethyl. In certain embodiments, $R^1$ is tert-butyl, cyclopropylmethyl or dicyclopropylmethyl, $R^2$ is Fmoc and $R^3$ and $R^4$ are a silyl-based hydroxyl protecting group. In certain embodiments, $R^1$ is tert-butyl, cyclopropylmethyl or dicyclopropylmethyl, $R^2$ is Fmoc and $R^3$ and $R^4$ are trialkylsilyl. In certain embodiments, $R^1$ is tert-butyl, cyclopropylmethyl or dicyclopropylmethyl, $R^2$ is Fmoc and $R^3$ and $R^4$ are trimethylsilyl. In certain embodiments, $R^1$ is tert-butyl, cyclopropylmethyl or dicyclopropylmethyl, $R^2$ is Fmoc and $R^3$ and $R^4$ together are a benzyl or a substituted phenylmethyl (e.g. p-methoxy benzylidene).

In certain embodiments, $R^2$ is fluorenylmethyloxycarbonyl (Fmoc).

In certain embodiments, $R^3$ and/or $R^4$ is selected from p-methoxy benzylidene, acetonide, and acetate.

The following compounds have proven to be of particular interest in reacting the title compound to amanitine derivatives:

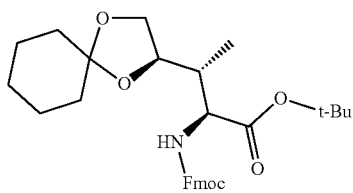

(2S,3R)-3-[(2R)-1,4-dioxaspiro[4.5]decane-2-yl]-2-(fluorenylmethyloxycarbonyl amino)butanoic acid tert.-butylester

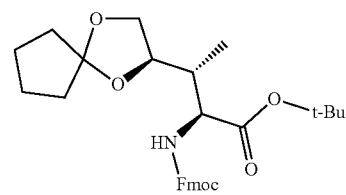

(2S,3R)-3-[(2R)-1,4-dioxaspiro[4.4]nonane-2-yl]-2-(fluorenylmethyloxycarbonyl amino)butanoic acid tert.-butylester

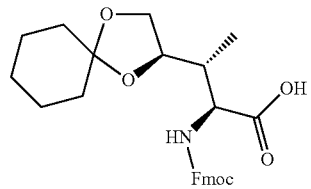

(2S,3R)-3-[(2R)-1,4-dioxaspiro[4.5]decane-2-yl]-2-(fluorenylmethyloxycarbonyl amino)butanoic acid

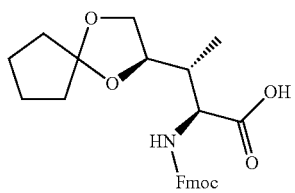

19

(2S,3R)-3-[(2R)-1,4-dioxaspiro[4.4]nonane-2-yl]-2-(fluorenylmethyloxycarbonyl amino)butanoic acid

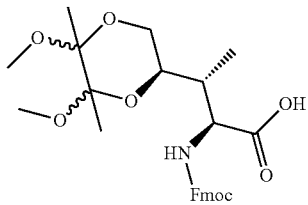

(2S,3R)-3-[(2R)-5,6-dimethoxy-5,6-dimethyl-1,4-dioxane-2-yl]-2-(fluorenylmethyloxycarbonyl amino)butanoic acid

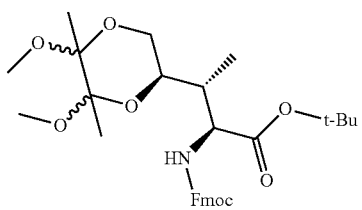

(2S,3R)-3-[(2R)-5,6-dimethoxy-5,6-dimethyl-1,4-dioxane-2-yl]-2-(fluorenylmethyloxycarbonyl amino)butanoic acid tert.butylester

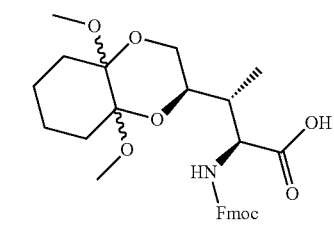

(2S,3R)-3-[(2R)-4a,8a-dimethoxy-2,3,5,6,7,8-octahydrobenzo[b][1,4]dioxin-2-yl]-2-(fluorenylmethyloxycarbonyl amino)butanoic acid

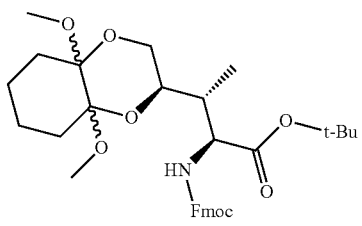

20

(2S,3R)-3-[(2R)-4a,8a-dimethoxy-2,3,5,6,7,8-octahydrobenzo[b][1,4]dioxin-2-yl]-2-(fluorenylmethyloxycarbonyl amino)butanoic acid tert-butylester

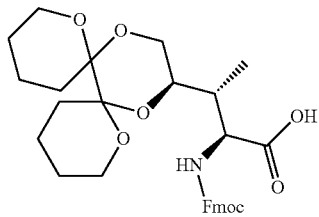

(2S,3R)-2-(fluorenylmethyloxycarbonylamino)-3-[(14R)-1,8,13,16-tetraoxadispiro[5.0.5.4]hexadecane-14-yl]butanoic acid

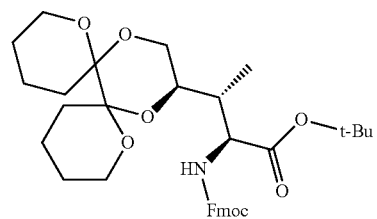

(2S,3R)-2-(fluorenylmethyloxycarbonylamino)-3-[(14R)-1,8,13,16-tetraoxadispiro[5.0.5.4]hexadecan-14-yl]butanoic acid tert-butylester

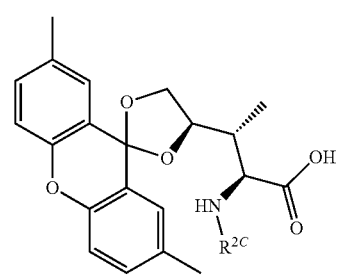

(2S,3R)-3-[(4R)-2',7'-dimethylspiro[1,3-dioxolane-2,9'-xanthene]-4-yl]-2-(fluorenylmethyloxycarbonylamino)butanoic acid

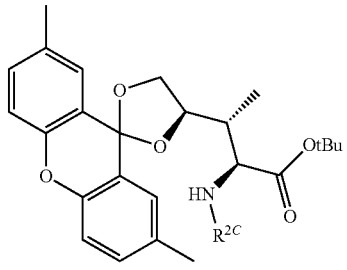

(2S,3R)-3-[(4R)-spiro[1,3-dioxolane-2,9'-xanthene]-4-yl]-2-(fluorenyl-methyloxycarbonylamino)butanoic acid t-butylester

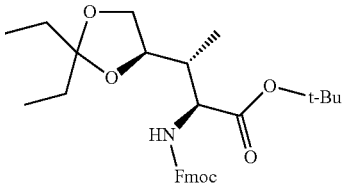

(2S,3R)-3-[(4R)-2,2-diethyl-1,3-dioxolan-4-yl]-2-(fluorenylmethyloxycarbonyl amino)butanoic acid t-butylester

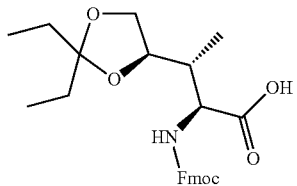

(2S,3R)-3-[(4R)-2,2-diethyl-1,3-dioxolan-4-yl]-2-(fluorenylmethyloxycarbonyl amino)butanoic acid

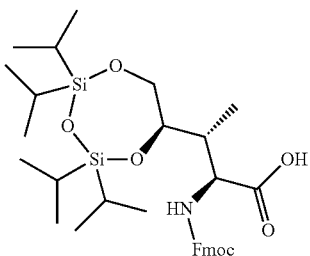

(2S,3R)-3-[2,2,4,4,-tetrakis (1-methylethyl)-1,3,5-trioxa-2,4-disiloxylheptane-2-yl-]2-(fluorenylmethyloxycarbonylamino)butanoic acid

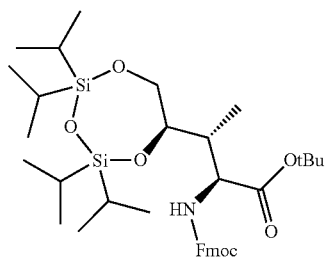

(2S,3R)-3-[2,2,4,4,-tetrakis (1-methylethyl)-1,3,5-trioxa-2,4-disiloxylheptane-2-yl-]2-(fluorenylmethyloxycarbonylamino)butanoic acid t-butylester In summary, the inventors have succeeded in synthesizing precursors of (2S,3R,4R)-4,5-dihydroxyisoleucine by Claisen rearrangement, providing a suitable scaffold amenable to asymmetric Sharpless dihydroxylation or Sharpless epoxidation followed by epoxide ring opening. Particularly advantageous results concerning the yield, enantiomeric excess and diastereoselectivity were achieved by using quinidine as chiral ligand during the asymmetric Claisen rearrangement. The Claisen rearrangement without the use of chiral ligands resulted in low yield of 4,5-didehydroisoleucine with no enantiomeric excess and long reaction times of up to four days. The undesired (R,R)- and (R,S)-configured stereoisomers were almost completely separated by enzymatic kinetic resolution using acylase from the desired (S,S)-enantiomer. The final diastereoselectivity between (S,S)- and (S,R)-4,5-didehydroisoleucine was calculated to be 94:6.

The present invention affords a valuable alternative to the synthesis route of EP2872479, facilitating gram scale synthesis of (2S,3R,4R)-4,5-dihydroxyisoleucine.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

Figure 1:
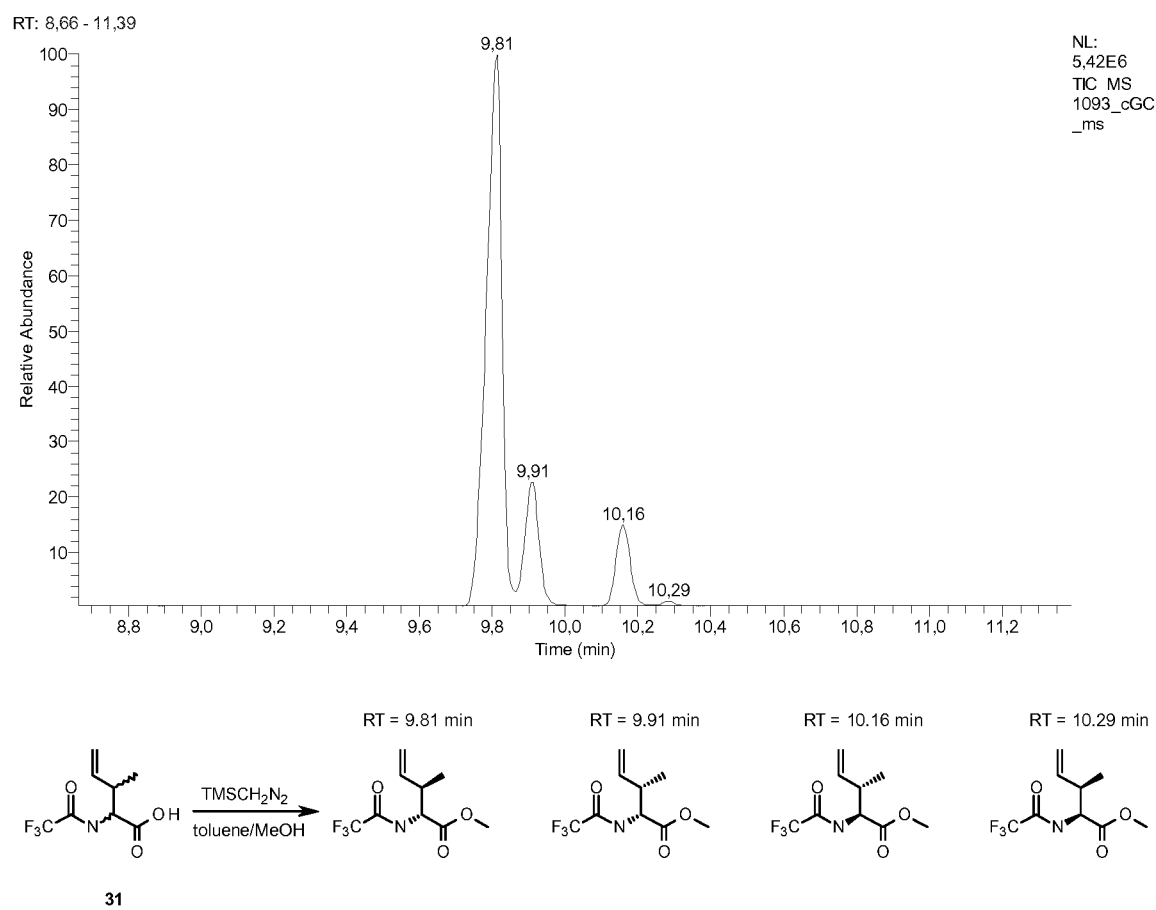
FIG. 1 a chiral GC-MS chromatogram of the methylated and TFA-protected 4,5-didehydroisoleucine after the asymmetric Claisen rearrangement with quinine as ligand.
Figure 2:
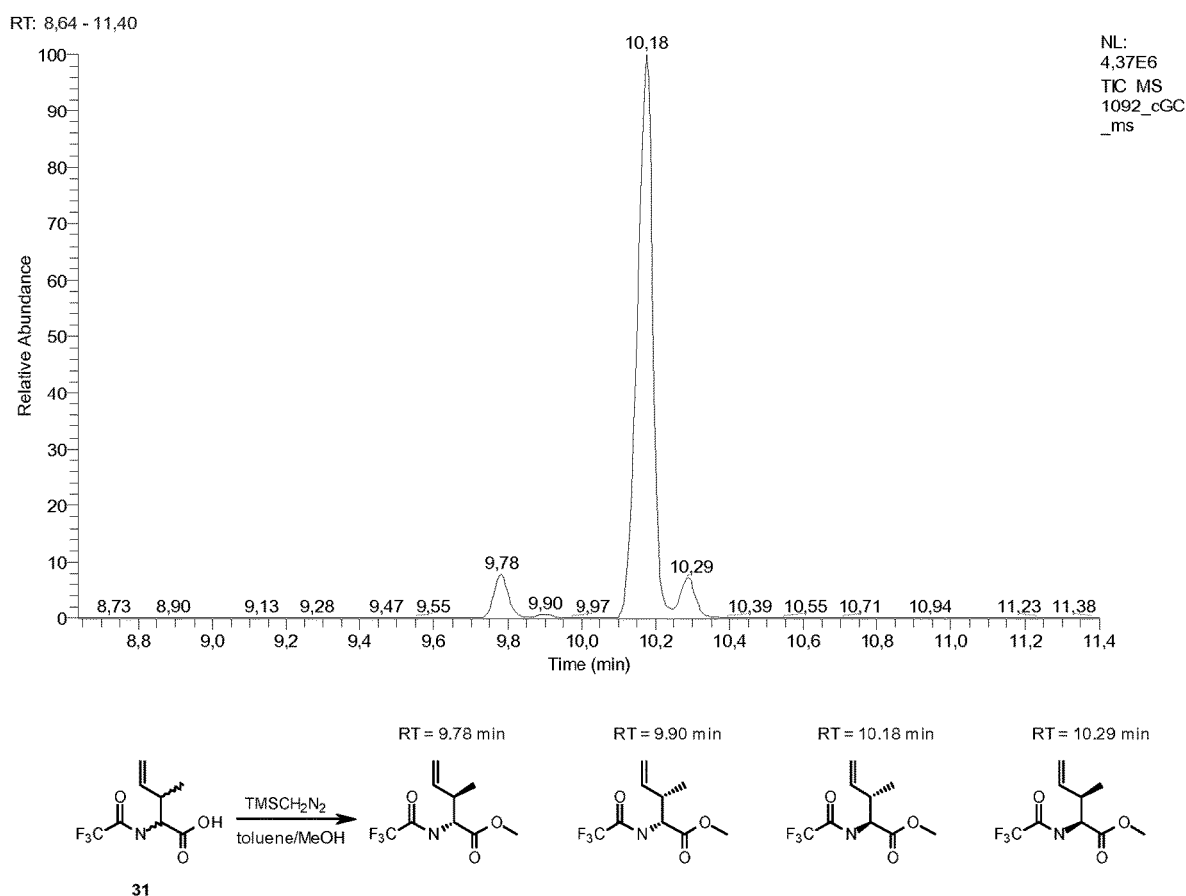
FIG. 2 shows a chiral GC-MS chromatogram of the methylated and TFA-protected 4,5-didehydroisoleucine after the asymmetric Claisen rearrangement with quinidine as ligand.
Figure 3:
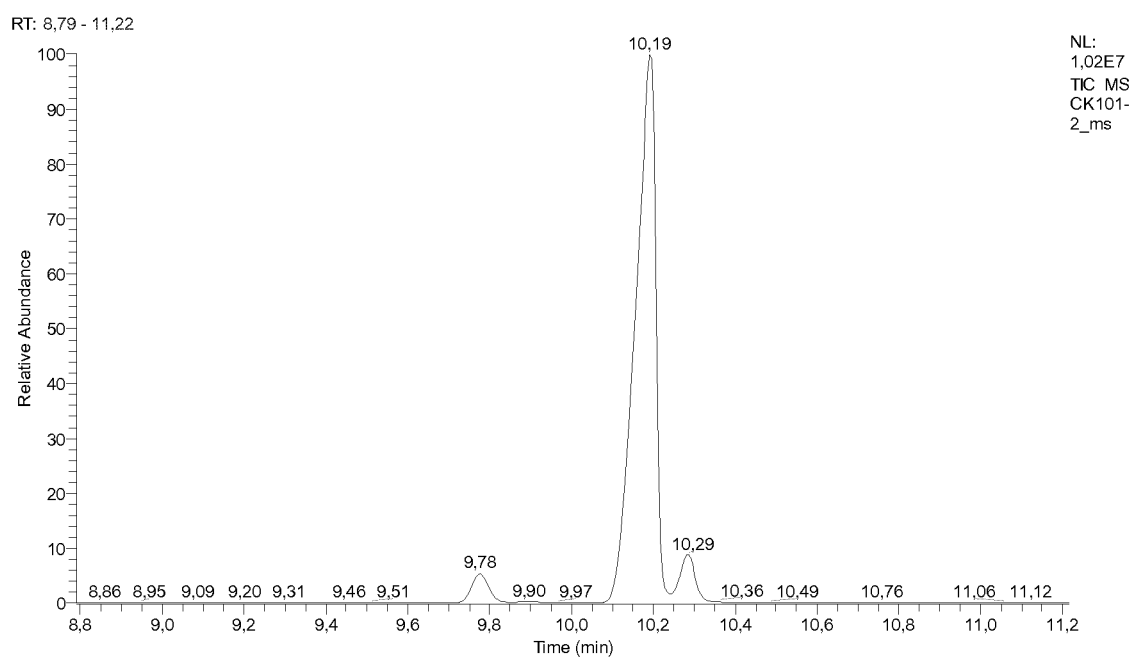
FIG. 3 shows a chiral GC-MS chromatogram of the trifluoroacetylated and methylated 4,5-didehydroisoleucine after enzymatic kinetic resolution of 31a-d.
Figure 3:
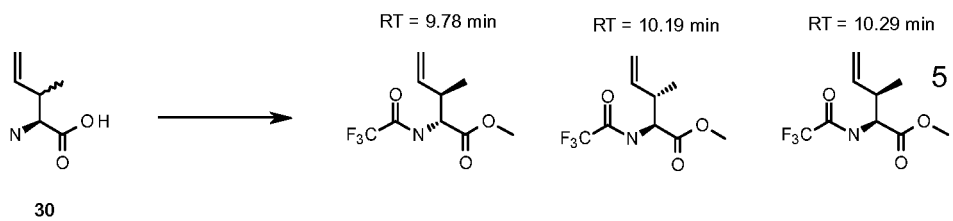
Figure 4:
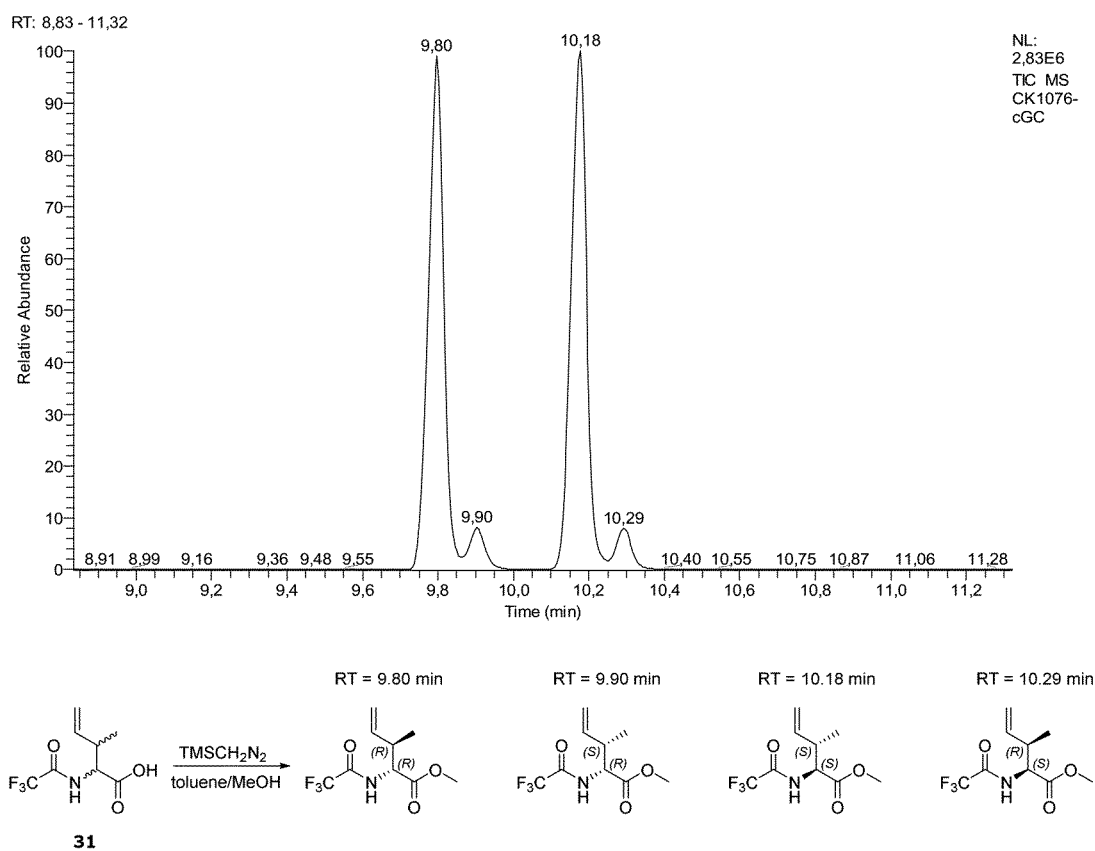
FIG. 4 shows a Chiral GC-MS chromatogram of the methylated and TFA-protected 4,5-didehydroisoleucine

General
Chemicals and Solvents

Chemicals and solvents were purchased from ABCR (Karlsruhe, Germany), ACROS ORGANICS (Geel, Belgium), ALFA AESAR (Karlsruhe, Germany), FLUKA (Buchs, Switzerland), FLUOROCHEM LIMITED (Derbyshire, UK), IRIS BIOTECH (Marktredwitz, Germany), CARL ROTH (Karlsruhe, Germany), MERCK (Darmstadt, Germany), NOVABIOCHEM (Darmstadt, Germany), BACHEM (Bubendorf, Switzerland) or SIGMA-ALDRICH (Taufkirchen, Germany) and used without further purification.

DMSO-$d_6$ (99.9%), CDCl$_3$ (99.9%) and D$_2$O (98.8%) for NMR spectroscopy were purchased from DEUTERO (Kastellaun, Germany) and SIGMA-ALDRICH (Taufkirchen, Germany).

Inert Gas

Reactions sensitive to air and moisture were carried out under argon atmosphere in oven-dried flasks. Liquid reactants were added with PE-syringes, which were flushed with argon several times, via septum. Solids were either dissolved and added as a solution or introduced into the reaction vessel as powder under a flow of argon.

Thin Layer Chromatography (TLC)

TLC was performed on silica plates purchased from MERCK (Silica gel 60 $F_{254}$). The compounds were detected by UV-irradiation ($\lambda$=254 nm) and the use of permanganate-, ninhydrin- and molybdate staining reagents.

Column Chromatography

Column chromatography was carried out on silica gel 40-63 µm purchased from GRACE DAVISON (Deerfield, USA) using pressurized air.

NMR Spectra $^1$H NMR and. $^{13}$C NMR spectra were measured on Bruker DRX 500 and AM 400 instruments. Chemical shifts δ are reported in parts per million (ppm) and relative to the remaining proton signals of CDCl$_3$ ($^1$H: δ=7.26 ppm; $^{13}$C: δ=77.16 ppm) and DMSO-d$_6$ ($^1$H: δ=2.5 ppm; $^{13}$C: δ=39.5 ppm). Coupling constants J are given in Hertz (Hz) and refer to H—H-coupling. Integrals are in accordance with assignments. Multiplicities: s=singulet, d=duplet, t=triplet, q=quartet. When the multiplicity could not be identified, the chemical shift range of the signal was given (m=multiplet). 13C NMR spectra are proton-decoupled.

Mass Spectra

LC-HRMS (ESI) was measured with Orbitrap XL-mass spectrometer from THERMO SCIENTIFIC (Waltham, Mass., USA) coupled with 1200-HPLC from AGILENT TECHNOLOGIES using a hypersil 100-C$_{18}$-column from THERMO SCIENTIFIC (solvent A: water/0.025% HCOOH, solvent B: AcN/0.025% HCOOH; flow rate: 1.3 ml/min). Xcalibur (THERMO SCIENTIFIC) was used for the evaluation of the spectra.

Chiral GC-MS

Chiral GC-MS was measured with 5975C from AGILENT TECHNOLOGIES) using a CS EnantioSELECT GC column (30 m, 250 µm×0.3 µm; CS Chromatographie Service GmbH, Langerwehe, Germany).

The temperature gradient (44 min) started with an initial hold for 2 min at 70° C. followed by an increase of 4° C./min up to 240° C. Scans were performed in electron impact (EI) mode (MS source: 300° C., MS Quad: 150° C., Emission: 108.8 µA, Energy: 50 eV) with a flow of 1.2 mL/min using helium as carrier gas.

Preparative HPLC

Purification by Preparative HPLC was performed with 1260 Infinity from AGILENT TECHNOLOGIEs using a PLRP-S column (partial size 10 µm×100 Å) from AGILENT TECHNOLOGIES. Used solvents were water and AcN, each with addition of 0.1% TFA.

(Z)-but-2-En-1-ol (10)

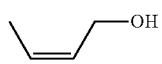

A solution of 12 ml but-2-yn-1-ol (10) (11.28 g, 160.94 mmol, 1.0 eq) in MeOH was degassed with nitrogen for 30 min. Then 1.2 g of Lindlar's catalyst (7.5 g/mmol) was added after which the reaction mixture was degassed with hydrogen for 1 h. After vigorous stirring at room temperature under 1.0 atm of hydrogen overnight the catalyst was filtered through a pad of Celite. Afterwards the mixture was concentrated and purified by distillation to obtain the product (10) (7.1 g, 98.6 mmol, 61%) as a transparent liquid.

HRMS (APCI): m/z calc for C$_4$H$_8$O [M+H]$^+$ 73.0648 found 73.0647.

$^1$H-NMR (400 MHz, CDCl$_3$): δ (ppm)=5.57-5.67 (m, 2H), 4.17-4.21 (m, 2H), 1.85 (s, 1H), 1.64-1.67 (m, 3H)

$^{13}$C-NMR (100 MHz, CDCl$_3$): δ (ppm)=129.35, 127.36, 58.40, 13.22

Trifluoroacetyl Glycine (11)

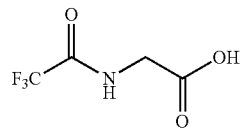

To a solution of glycine (2.5 g, 33.3 mmol, 1.0 eq) in MeOH triethylamine (4.6 ml, 33.3 mmol, 1.0 eq) was added dropwise. After stirring for 5 min ethyl trifluoroacetate (5.2 ml, 43.3 mmol, 1.3 eq) was added and the mixture was stirred for 16 h at room temperature during which time a clear solution formed. Then the reaction mixture was concentrated under reduced pressure and the resulting residue acidified with 2 N HCl before being extracted with EtOAc (3×75 ml). The organic layers were combined then washed with brine and dried over MgSO$_4$. The solvent was removed in vacuo to give the product (11) as a white crystalline solid (5.4 g, 31.6 mmol, 95%).

HRMS (ESI): m/z calc for C$_4$H$_4$F$_3$NO$_3$[M−H]$^-$ 170.0060 found 170.0073.

DC (n-Hexan/EtOAc/n-Bu/H$_2$O/AcOH, 2:1:1:1): $R_f$=0.6.

$^1$H-NMR (400 MHz, CDCl$_3$): δ (ppm)=12.97 (br, 1H), 9.85 (t, J=6.0 Hz, 1H), 3.92 (d, J=6.0 Hz, 2H)

$^{13}$C-NMR (100 MHz, CDCl$_3$): δ (ppm)=169.96, 156.87, 117.61, 41.08

(Z)-but-2-Enyl Trifluoroacetyl Glycinate (21)

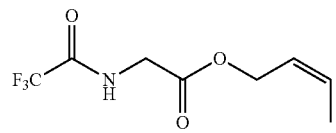

DCC (14.9 g, 72.1 mmol, 1.3 eq) and DMAP (0.7 g, 5.6 mmol, 0.1 eq) were added to a solution of the allylic alcohol (10) (4.0 g, 55.5 mmol, 1.0 eq) in DCM at 0° C. The solution was cooled to −20° C. and the TFA-protected amino acid (11) (11.4 g, 66.6 mmol, 1.2 eq) was added after 5 min. The reaction mixture was allowed to warm to room temperature overnight. After filtration of the DCU and washing of the precipitate with cold DCM the organic phase was washed with 1N HCl (2×200 ml), saturated NaHCO$_3$ (1×200 ml) and brine (1×200 ml). The organic layer was dried with MgSO$_4$ and evaporated in vacuo. After purification by flash column chromatography on silica gel (hexane/ethyl acetate, 4:1) the product (21) was obtained as light yellow crystals (11.2 g, 49.9 mmol, 90%).

HRMS (ESI): m/z calc for $C_8H_{10}F_3NO_3[M+H]^+$ 226.0686 found 226.0681.

DC (n-Hexan/EtOAc, 4:1): $R_f$=0.4.

$^1$H-NMR (400 MHz, CDCl$_3$): δ (ppm)=6.94 (br, 1H), 5.74-5.84 (m, 1H), 5.51-5.60 (m, 1H), 4.76 (d, J=7.05 Hz, 2H), 4.13 (d, J=5.1 Hz, 2H), 1.72 (dd, J=7.1, 1.6 Hz, 3H)

$^{13}$C-NMR (100 MHz, CDCl$_3$): δ (ppm)=176.98, 160.81, 83.29, 66.67, 61.57, 56.92, 33.45, 32.01

Boc-Glycine (18)

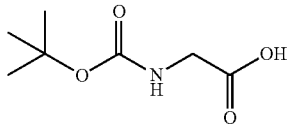

Glycine (10 g, 133.2 mmol, 1.0 eq) and NaHCO$_3$ (33.6 g, 399.6 mmol, 3.0 eq) were dissolved in a 1:2 mixture of water/dioxane. Then Boc$_2$O was added dropwise and the reaction mixture of stirred at room temperature for 16 h. After concentrating the mixture under reduced pressure the resultant residue was diluted with water until the precipitate was dissolved and then acidified with 1N HCl to pH 3. Afterwards the aqueous solution was extracted with EtOAc (3×250 ml). The organic layers were combined then washed with brine and dried over MgSO$_4$. The solvent was removed in vacuo to give the product (18) as a white crystalline solid (20.7 g, 118.0 mmol, 87%).

HRMS (ESI): m/z calc for $C_7H_{13}NO_4[M+H]^+$ 176.0917 found 176.0919 [M+Na]$^+$ 198.0737 found 198.0738.

TLC (n-Hexan/EtOAc/n-Bu/H$_2$O/AcOH, 2:1:1:1): $R_f$=0.9

$^1$H-NMR (400 MHz, CDCl$_3$): δ (ppm)=3.84-3.98 (m, 2H), 1.44 (s, 9H)

$^{13}$C-NMR (100 MHz, CDCl$_3$): δ (ppm)=174.21, 156.34, 80.63, 42.44, 28.65

(Z)-but-2-Enyl Boc-Glycinate (29)

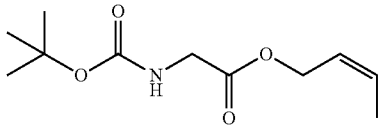

DCC (3.7 g, 18.0 mmol, 1.3 eq) and DMAP (0.2 g, 1.4 mmol, 0.1 eq) were added to a solution of the allylic alcohol (10) (1.0 g, 13.9 mmol, 1.0 eq) in DCM at 0° C. The solution was cooled to −20° C. and the boc-protected amino acid (18) (2.7 g, 15.3 mmol, 1.2 eq) was added after 5 min. The reaction mixture was allowed to warm to room temperature overnight. After filtration of the DCU and washing of the precipitate with cold DCM the organic phase was washed with 1N HCl (2×150 ml), saturated NaHCO$_3$ (1×150 ml) and brine (1×150 ml). The organic layer was dried with MgSO$_4$ and evaporated in vacuo. After purification by column chromatography (hexane/ethyl acetate, 4:1) the product (29) was obtained as a colourless oil (2.6 g, 11.1 mmol, 80%)

HRMS (ESI): m/z calc for $C_{11}H_{19}NO_4[M+H]^+$ 231.1420 found 231.1422 [M+Na]$^+$ 252.1206 found 252.1207.

TLC (n-Hexan/EtOAc, 5:1): $R_f$=0.3

$^1$H-NMR (400 MHz, CDCl$_3$): δ (ppm)=5.67-5.77 (m, 1H), 5.47-5.57 (m, 1H), 5.06 (br, 1H), 4.69 (d, J=7.2 Hz, 2H), 3.89 (s, 2H), 1.69 (d, J=7.0 Hz, 3H), 1.43 (s, 9H)

$^{13}$C-NMR (100 MHz, CDCl$_3$): δ (ppm)=170.75, 156.04, 130.46, 123.90, 79.94, 61.07, 42.67, 28.46, 13.27

(Z)-but-2-Enyl Cbz-Glycinate (29x)

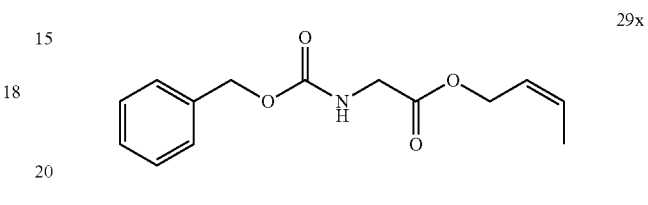

DCC (3.7 g, 72.1 mmol, 1.3 eq) and DMAP (0.2 g, 1.4 mmol, 0.1 eq) were added to a solution of the allylic alcohol (10) (1.0 g, 13.9 mmol, 1.0 eq) in DCM at 0° C. The solution was cooled to −20° C. and the cbz-protected amino acid (3.3 g, 15.3 mmol, 1.2 eq) was added after 5 min. The reaction mixture was allowed to warm to room temperature overnight. After filtration of the DCU and washing of the precipitate with cold DCM the organic phase was washed with 1N HCl (2×150 ml), saturated NaHCO$_3$ (1×150 ml) and brine (1×150 ml). The organic layer was dried with MgSO$_4$ and evaporated in vacuo. After purification by column chromatography (hexane/ethyl acetate, 4:1) the product was obtained as a colourless oil (2.7 g, 10.4 mmol, 75%).

HRMS (ESI): m/z calc for $C_{14}H_{17}NO_4[M+H]^+$ 264.1230 found 264.1223 [M+Na]$^+$ 286.1050 found 286.1043.

TLC (n-Hexan/EtOAc, 5:1): $R_f$=0.3

$^1$H-NMR (400 MHz, CDCl$_3$): δ (ppm)=7.20-7.29 (m, 5H), 5.61-5.71 (m, 1H), 5.40-5.50 (m, 1H), 5.24 (br, 1H), 5.04 (s, 2H), 4.43 (d, J=7.2 Hz, 2H), 3.89 (d, J=5.6 Hz, 2H), 1.61 (d, J=7.0 Hz, 3H)

$^{13}$C-NMR (100 MHz, CDCl$_3$): δ (ppm)=170.26, 156.65, 136.39, 130.67, 128.69, 128.35, 128.25, 123.87, 67.42, 61.08, 42.99, 13.45

Trifluoroacetyl Didehydroisoleucine (31)

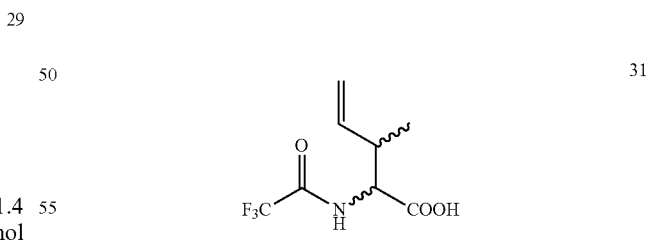

A LHMDS solution was freshly prepared by adding 2.5 M nBuLi in hexane (8.9 ml, 22.2 mmol, 1.0 eq) to hexamethyldisilazane (4.3 g, 26.7 mmol, 1.2 eq) in 7.76 ml dry THF at −20° C. under argon atmosphere. The trifluoroacetyl protected glycine crotyl ester (21) (1.0 g, 4.4 mmol, 1.0 eq) and dry zinc chloride (1.2 g, 8.9 mmol, 2.0 eq) were dissolved in 8 ml dry THF and cooled to −78° C. Then the previously prepared LHMDS solution was added slowly. The reaction mixture was allowed to warm to room temperature overnight and stirred for 3 d. After diluting with EtO₂ (200 ml) the reaction mixture was hydrolyzed by addition of 1 N KHSO₄ until the precipitate was fully dissolved in the organic layer. Then the reaction mixture was extracted with saturated NaHCO₃ (3×100 ml). Afterwards the basic aqueous solution was acidified by careful addition of solid KHSO₄ to pH 1 and extracted with EtO₂ (3×50 ml). The combined organic layers were dried over MgSO₄ and the solvent was evaporated in vacuo. The product (31) was obtained as a yellow oil (700.1 mg, 3.1 mmol, 70%). For the determination of the enantiomeric and diastereomeric ratios of the product, the residue was treated with trimethylsilyl diazomethane in ether solution.

HRMS (ESI): m/z calc for $C_8H_9F_3NO_3[M-H]^-$ 224.0529 found 224.0536.

TLC (n-Hexan/EtOAc/n-Bu/H₂O/AcOH, 2:1:1:1): $R_f$=0.95

¹H-NMR (400 MHz, CDCl₃): δ (ppm)=6.63 (br, 1H), 5.66-5.77 (m, 1H) 5.19-5.27 (m, 2H), 4.66 (q, J=4.2 Hz, 1H), 2.90-2.99 (m, 1H), 1.15 (d, J=7.04 Hz, 3H)

¹³C-NMR (100 MHz, CDCl₃): δ (ppm)=175.37, 157.67, 136.37, 118.37, 117.00, 56.43, 39.56, 16.32

Trifluoroacetyl Didehydroisoleucine (31)

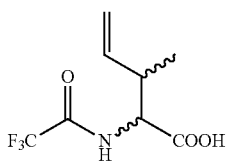

The trifluoroacetyl protected glycine crotyl ester (21) (1.0 eq), dry aluminium isopropoxide (1.25 eq) and quinidine (2.5 eq) were dissolved in dry THF and cooled to −78° C. Then, LHMDS (1 M in THF, 5.5 eq) was added slowly. The reaction mixture was allowed to warm to room temperature overnight and stirred for 2 d. After diluting with EtO₂ the reaction mixture was hydrolyzed by addition of 1 M KHSO₄ until the precipitate was fully dissolved in the organic layer. Then the reaction mixture was extracted with saturated NaHCO₃. Afterwards the basic aqueous solution was acidified by careful addition of solid KHSO₄ to pH 1 and extracted with EtO₂. The combined organic layers were dried over MgSO₄ and the solvent was evaporated in vacuo. The rearrangement product (31) was obtained as a yellow oil (72%). For the determination of the enantiomeric and diastereomeric ratios of the product, the residue was treated with trimethylsilyl diazomethane in ether solution.

Boc-4,5-Didehydroisoleucine (39)

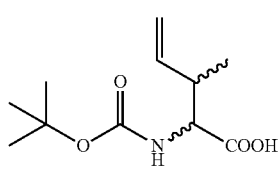

A LHMDS solution was freshly prepared by adding 2.5 M nBuLi in hexane (7.0 ml, 17.5 mmol, 1.0 eq) to hexamethyldisilazane (3.4 g, 20.9 mmol, 1.2 eq) in 6.1 ml dry THF at −20° C. under argon atmosphere. The Boc-protected glycine crotyl ester (83) (800.0 mg, 3.5 mmol, 1.0 eq) and dry zinc chloride (951.0 g, 8.9 mmol, 2.0 eq) were dissolved in 7 ml dry THF and cooled to −78° C. Then the previously prepared LHMDS solution was added slowly. The reaction mixture was allowed to warm to room temperature overnight and stirred for 3 d. After diluting with EtO₂ (200 ml) the reaction mixture was hydrolyzed by addition of 1N KHSO₄ until the precipitate was fully dissolved in the organic layer. Then the reaction mixture was extracted with saturated NaHCO₃ (3×100 ml). Afterwards the basic aqueous solution was acidified by careful addition of solid KHSO₄ to pH 1 and extracted with EtO₂ (3×50 ml). The combined organic layers were dried over MgSO₄ and the solvent was evaporated in vacuo. After purification by flash column chromatography (dichloromethane/2% methanol) the product (39) was obtained as pale yellow oil (267.2 mg, 1.2 mmol, 34%).

HRMS (ESI): m/z calc for $C_8H_9F_3NO_3[M-H]^-$ 224.0529 found 224.0536.

TLC (n-Hexan/EtOAc/n-Bu/H₂O/AcOH, 2:1:1:1): $R_f$=0.95

¹H-NMR (400 MHz, CDCl₃): δ (ppm)=6.63 (br, 1H), 5.66-5.77 (m, 1H) 5.19-5.27 (m, 2H), 4.66 (q, J=4.2 Hz, 1H), 2.90-2.99 (m, 1H), 1.15 (d, J=7.04 Hz, 3H)

¹³C-NMR (100 MHz, CDCl₃): δ (ppm)=175.37, 157.67, 136.37, 118.37, 117.00, 56.43, 39.56, 16.32

Trifluoroacetyl 4,5-Didehydroisoleucine Methyl Ester

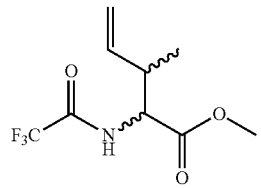 [SMILES: C=CC(C)C(NC(=O)C(F)(F)F)C(=O)OC]

Trifluoroacetyl 4,5-didehydroisoleucine (67) (30.0 mg, 133.2 μmol, 1.0 eq) was dissolved in a 1:1 mixture of MeOH/toluol. Then trimethylsilyl diazomethane (15.2 mg, 0.1 mmol, 1.0 eq) was added dropwise and the reaction mixture of stirred at room temperature for 30 min. After evaporation of the solvent under reduced pressure the resultant the crude product was purified by column chromatography on silica gel (hexane/ethyl acetate, 5:1) to give the product as a colourless oil (29.5 mg, 123.3 μmol, 93%).

TLC (n-Hexan/EtOAc, 4:1): $R_f$=0.6

¹H-NMR (400 MHz, CDCl₃): δ (ppm)=6.68 (br, 1H), 5.62-5.72 (m, 1H) 5.11-5.21 (m, 2H), 4.61 (q, J=4.2 Hz, 1H), 3.80 (s, 3H), 2.81-2.90 (m, 1H), 1.11 (d, J=7.2 Hz, 3H)

¹³C-NMR (100 MHz, CDCl₃): δ (ppm)=170.67, 157.39, 136.92, 118.11, 114.24, 56.98, 53.11, 40.38, 16.04

N-Acetyl 4,5-Didehydroisoleucine (32)

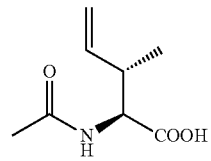

The trifluoroacetylated amino acid (31) (375.0 mg, 1.7 mmol, 1.0 eq) was dissolved in 8 ml MeOH and K$_2$CO$_3$ (1153.9 mg, 8.4 mmol, 5 eq) was added. Then the reaction mixture was refluxed for 2 hours until the deprotection was complete which was monitored by TLC. Afterwards the mixture was filtered to remove the K$_2$CO$_3$. The solvent was removed under reduced pressure and the resulting residue was dissolved in 8 ml THF. Then acetic anhydride (787.8 µl, 8.4 mmol, 3.0 eq) was added dropwise. After the reaction mixture was refluxed for 6 hours the solvent was removed in vacuo. After purification by flash column chromatography (dichloromethane/5% methanol) the product (91) was obtained as a brown oil (260.0 mg, 1.5 mmol, 90%).

HRMS (ESI): m/z calc for C8H13NO3 [MH]$^-$ 170.0812 found 170.0819.

TLC (n-Hexan/EtOAc/n-Bu/H$_2$O/AcOH, 2:1:1:1): R$_f$=0.98

$^1$H-NMR (400 MHz, DMSO-d$_6$): δ (ppm)=7.98 (t, J=9.96 Hz, 1H), 5.68-5.83 (m, 1H) 4.96-5.08 (m, 2H), 4.30-4.22 (m, 1H), 2.56-2.66 (m, 1H), 1.83-1.92 (m, 3H), 0.97 (dd, J=4.4, 2.7 Hz 3H)

$^{13}$C-NMR (100 MHz, DMSO-d$_6$): δ (ppm)=173.01, 169.63, 139.92, 115.34, 56.38, 22.49, 16.87, 15.26

4,5-Didehydroisoleucine (30)

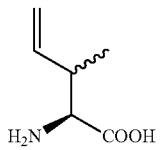

To a solution of racemic N-acetylated 2-amino-3-methylpentanoic acid (1412.4 mg, 8.3 mmol, 1.0 eq) in 0.1 M phosphate buffer (30 ml, pH 7.5) and 4 M KOH (2.1 ml, 8.3 mmol, 1.0 eq) acylase I from *Aspergillus melleus* (700 mg) was added. After 6 h at 35° C. the reaction mixture was acidified to pH 3 and filtered through a PTFE membrane filter (pore size 0.2 µm). Afterwards the filtrate was extracted with diethylether (3×20 ml) and concentrated in vacuo. The crude product was submitted to the next reaction step without further purification.

HRMS (ESI): m/z calc for C$_6$H$_{11}$NO$_2$[M+H]$^+$ 130.0863 found 130.0858. [M+Na]$^+$ 152.0682 found 152.0680.

TLC (n-Hexan/EtOAc/n-Bu/H$_2$O/AcOH, 2:1:1:1): R$_f$=0.45

Fmoc-4,5-Didehydroisoleucine (35)

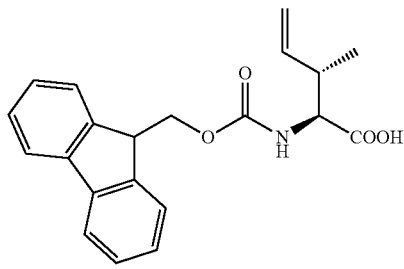

To a stirring solution of 4,5-didehydroisoleucine 30 (300.0 mg, 2.32 mmol, 1.0 eq) in 10 ml of a 1:1 mixture of water/acetonitrile, NaHCO$_3$ (585.4 mg, 6.9 mmol, 3.0 eq) and Fmoc-OSu (1020.0 mg, 3.02 mmol, 1.3 eq) were added. After stirring for 16 h the reaction mixture was diluted with 50 ml water, acidified to pH 2 with 1 N HCl and extracted with ethyl acetate (3×30 ml). The combined organic layers were washed with brine, dried over MgSO$_4$ and concentrated in vacuo. The crude product was purified by column chromatography on silica gel (dichloromethane/5% methanol) to obtain the Fmoc-protected amino acid 35 as a white crystalline solid (700.0 mg, 2.0 mmol, 86%).

HRMS (ESI): m/z calc for C$_{21}$H$_{21}$NO$_4$[M+H]$^+$ 374.1363 found 374.1360.

TLC (n-Hexan/EtOAc/n-Bu/H$_2$O/AcOH, 2:1:1:1): R$_f$=0.9

$^1$H-NMR (400 MHz, DMSO-d$_6$): δ (ppm)=8.49 (br, 1H), 7.68 (d, J=7.5 Hz, 2H), 7.44-7.54 (m, 2H), 7.32 (t, J=7.02 Hz, 2H), 7.23 (t, J=7.02 Hz, 2H), 5.45-5.73 (m, 1H), 5.18-5.32 (m, 1H), 5.01-5.17 (m, 1H), 4.30-4.37 (m, 2H), 4.12-4.19 (m, 1H), 2.39-2.54 (m, 1H), 2.44-2.52 (m, 1H), 1.60 (d, J=6.0 Hz, 2H), 1.05 (d, J=7.0 Hz, 1H)

$^{13}$C-NMR (100 MHz, DMSO-d$_6$): δ (ppm)=177.01, 156.04, 143.58, 141.45, 137.20, 130.67, 127.93, 127.02, 125.20, 124.13, 120.18, 117.60, 67.46, 58.04, 53.33, 47.25, 39.65, 35.09

Fmoc-4,5-Didehydroisoleucine Tert-Butyl Ester (36)

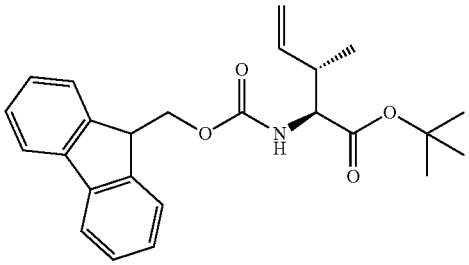

p-Toluenesulfonyl chloride (244.1 mg, 1.3 mmol, 1.5 eq) was added to a stirring solution of Fmoc-protected 4,5-didehydroisoleucine (35) (300.0 mg, 0.8 mmol, 1.0 eq) in 3 ml pyridine. The reaction mixture was cooled to 0° C. and tert-butanol (160.0 µl, 1.7 mmol, 2.0 eq) was added and allowed to warm to room temperature overnight. After stirring for 16 h dichloromethane (100 ml) was added. The organic solution was washed with 1 N HCl (3×50 ml) and evaporated in vacuo. The crude product was purified by column chromatography on silica gel (hexane/ethyl acetate, 10:1) to obtain the fully protected amino acid 36 as a colourless oil (200.5 mg, 0.5 mmol, 57%).

HRMS (ESI): m/z calc for C$_{25}$H$_{29}$NO$_4$[M+H]$^+$ 442.2224 found 442.2230.

TLC (n-Hexan/EtOAc, 10:1): R$_f$=0.3.

$^1$H-NMR (400 MHz, CDCl$_3$): δ (ppm)=7.68 (d, J=7.5 Hz, 2H), 7.52 (d, J=7.5 Hz, 2H), 7.31 (t, J=7.2 Hz, 2H), 7.22 (t, J=7.2 Hz, 2H), 5.59-5.69 (m, 1H), 5.12-5.19 (m, 1H), 4.99-5.09 (m, 2H), 4.25-4.34 (m, 2H), 4.12-4.25 (m, 2H), 2.64-2.76 (m, 1H), 1.39 (s, 9H), 1.01 (d, J=6.9 Hz, 3H), $^{13}$C-NMR (100 MHz, CDCl$_3$): δ (ppm)=170.63, 156.50, 144.04, 141.76, 137.96, 127.93, 127.02, 125.20, 125.20, 120.18, 116.69, 82.35, 67.15 58.34, 47.10, 40.56, 16.02

Fmoc-4,5-Dihydroxyisoleucine Tert-Butyl Ester (46)

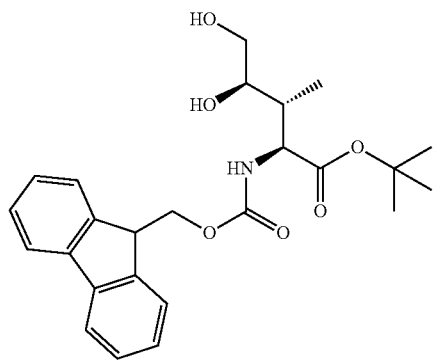

Terminal alkene 36 (177.0 mg, 0.4 mmol, 1.0 eq) was dissolved in 2.7 ml of a 1:1 mixture of water/t-BuOH, then AD-mix-ß (1120.0 mg, 2800 mg/mmol; Aldrich catalogue no. 392766) was added. After stirring vigorously for 16 h, the reaction was terminated by adding $Na_2SO_3$ (600.0 mg, 1500 mg/mmol). The mixture was then diluted with 30 ml of water and extracted with ethyl acetate (3×20 ml). The combined organic phases were washed with brine, dried over $Na_2SO_4$ and evaporated under reduced pressure. The crude product was purified by column chromatography on silica gel (dichloromethane/5% methanol) to obtain the dihydroxylated amino acid 46 as a white powder (7.9 mg, 17.9 μmol, 4%).

HRMS (ESI): m/z calc for $C_{25}H_{31}NO_6[M+H]^+$ 1104.5468 found 1104.5454 [M+Na]$^+$ 464.2044 found 464.2046.

Fmoc-4,5-Didehydroisoleucine Dicyclopropylmethyl Ester (47)

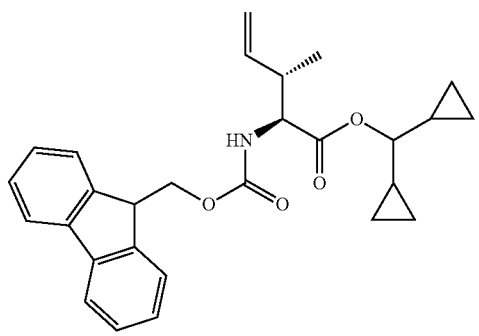

Compound 30a (860 mg, 2.4 mmol, 1.0 eq) was dissolved in 10 ml dichloromethane and treated with DMAP (30 mg, 0.24 mmol, 0.1 eq), EDC×HCl (910 mg, 4.7 mmol, 1.9 eq) and with dicyclopropylmethyl alcohol (420 mg, 3.7 mmol, 1.5 eq). The solution was stirred for 24 hours at 22° C. The solvent was removed under reduced pressure and the residue was taken up in 20 ml methyl tert-butyl ether (MTBE) and 20 ml water. The organic layer was washed with water (3×20 ml), dried over $MgSO_4$ and the solvent was evaporated in vacuum. The crude was purified via column chromatography on silica gel (iso-hexane/MTBE 4:1 (v/v)) to obtain the desired product 47 as a colorless oil (600 mg, 1.3 mmol, 56%).

MS (ESI): m/z calc for $C_{28}H_{31}NO_4[m+H]^+$ 446.23 found 446.21 [m+H]$^+$.

Fmoc-4,5-Dihydroxyisoleucine Dicyclopropylmethyl Ester (48)

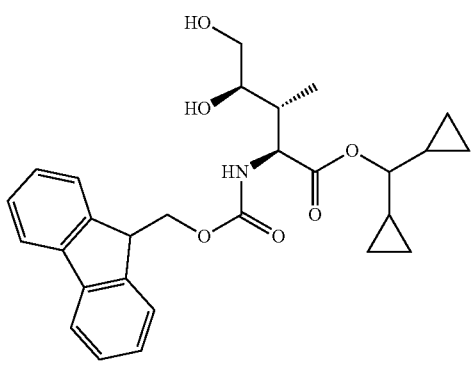

The full protected Fmoc-4,5-didehydroisoleucine derivative 47 (255 mg, 0.57 mmol, 1 eq) was dissolved in 12 ml of a 1:1 mixture (v/v) $CHCl_3/H_2O$, treated with AD-mix-ß (1596.0 mg, 2800 mg/mmol; Aldrich catalogue no. 392766) and stirred for 72 hours at 22° C. After no starting material was detectable (IPC via HPLC-MS) the solution was filtered and the two layers were separated. The organic layer was dried over $MgSO_4$ and the solvent was evaporated in vacuum. Finally, 260 mg crude of 48 (0.54 mmol, crude yield 95%) were obtained and the residue was used without further purification in subsequent reactions.

MS (ESI): m/z calc for $C_{28}H_{34}NO_6[m+H]^+$ 480.29 found 480.18 [M+H]$^+$ and 502.18 [M+Na]$^+$.

Fmoc-4,5-dioxy(tetra-isopropyl-disiloxane)isoleucine dicyclopropylmethyl ester (49)

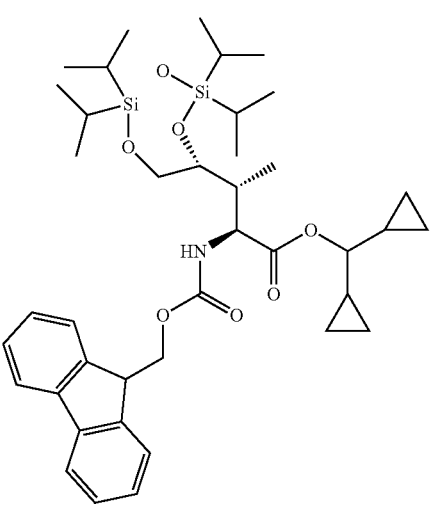

Substance 48 (260 mg, 0.54 mmol, 1 eq) was dissolved in 5 ml dry DMF and treated with imidazole (155 mg, 2.3 mmol, 4.2 eq) and 1,3-dichloro-tetra-isopropyl-disiloxane (341 mg, 1.08 mmol, 2 eq). The solution was stirred for 16 hours at 22° C. After the IPC (HPLC-MS) showed a full conversion 20 ml EtOAc and 20 ml water were added to the reaction solution. The layers were separated and the water layer was extracted with EtOAc (3×20 ml) again. The combined organic layers were dried over $MgSO_4$ and the solvent was removed under vacuum. The obtained residue of 49 was used without further purification for the subsequent de-protection reaction.

MS (ESI): m/z calc for $C_{40}H_{60}NO_7Si_2[M+H]^+$ 722.39 found 722.31 $[M+H]^+$ and 744.31 $[M+Na]^+$.

Fmoc-4,5-dioxy(tetra-isopropyl-disiloxane)isoleucine (50)

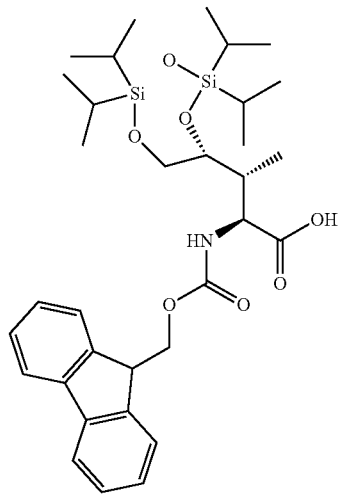

(50)

The crude of 49 (0.54 mmol), from the diol protection reaction, was dissolved in 10 ml 0.03 N HCl/dioxane and stirred for 48 hours at 22° C. After the mentioned duration, the IPC (HPLC-MS) showed full conversion to the desired target molecule. Therefore, the solvent was removed under reduced pressure and the residue was purified by silica gel column chromatography ($CH_2Cl_2$/MeOH/AcOH 190:10:1 (v/v/v)) to obtain the desired amino acid derivative 50 (218 mg, 0.3 mmol, 53%) as a colourless to slightly yellow oil.

MS (ESI): m/z calc for $C_{33}H_{50}NO_7Si_2[M+H]^+$ 628.31 found 628.23 $[M+H]^+$.

TLC ($CH_2Cl_2$/MeOH/AcOH 190:10:1): $R_f$=0.24

The invention claimed is:

1. A method for the preparation of a (2S,3R, 4R)-4,5-dihydroxyisoleucine derivative (400)

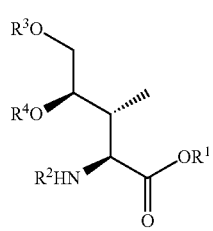

(400)

wherein:
$R^1$ is H or a carboxylic acid moiety protecting group,
$R^2$ is H or an amino moiety protecting group and
$R^3$ and $R^4$ are independently from another selected from H and a hydroxyl moiety protecting group, or both $R^3$ and $R^4$ are one single vicinal diol protecting group moiety, from a crotyl glycinester derivative (200), wherein said method comprises the method for the preparation of

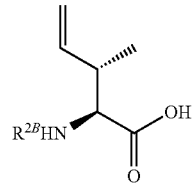

(310)

is converted to yield (2S,3S)-2-amino-3-methylpent-4-enoic acid (30)
(2S,3S)-2-amino-3-methylpent-4-enoic acid (30),

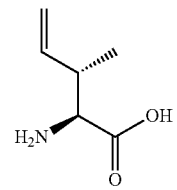

(30)

wherein said method comprises
a) the Claisen rearrangement step of reacting a Z-crotyl-glycin ester derivative 200

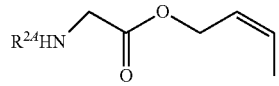

(200)

wherein $R^{2A}$ is amino protecting group stable under conditions favourable to Claisen rearrangement,
in the presence of a chiral ligand to yield 2-amino-3-methylpent-4-enoic acid derivative (300)

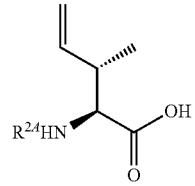

(300)

and
b) an enzymatic resolution step, wherein 2-amino-3-methylpent-4-enoic acid derivative (310) and further comprises
a) a Sharpless dihydroxylation step, wherein 2-amino-3-methylpent-4-enoic acid derivative (330)

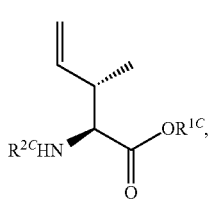 (330)

is reacted in the presence of Os(VIII) complexed by a chiral ligand, particularly by hydroquinidine 1,4-phthalazinediyl diether, to the 2-amino-3-methyl-4,5-dihydroxypentanoic acid derivative (430)

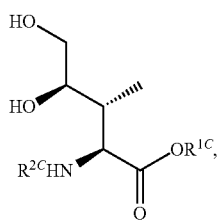 (430)

or b) a Sharpless epoxidation step, wherein 2-amino-3-methylpent-4-enoic acid derivative (330)

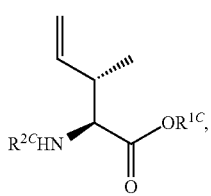 (330)

is reacted in the presence of a chiral ligand and a catalyst comprising titanium isopropoxide to a (2S,3S, 4R)-2-amino-3-methyl-4,5-epoxy-pentanoic acid derivative (360),

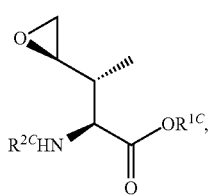 (360)

and and subsequent enzymatic conversion catalysed by an epoxide hydrolase into 2-amino-3-methyl-4,5-dihydroxy-pentanoic acid derivative (430),

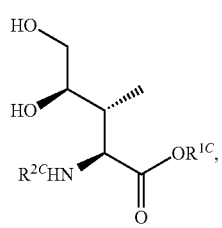 (430)

and wherein optionally, subsequent to step a) or b), any amino group protecting moiety $R^{2C}$ and/or carboxylic acid group protecting moiety $R^{1C}$ is selectively removed from (430) to yield the free (2S,3R, 4R)-4,5-dihydroxyisoleucine, or (430) is reacted with a vicinal diol protecting group, particularly to yield a compound selected from

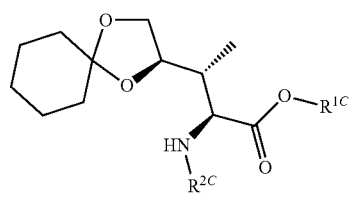

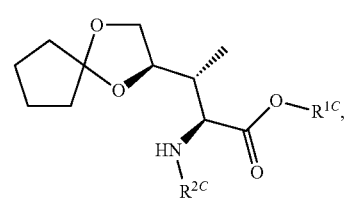

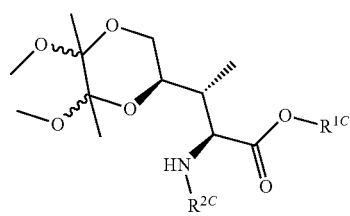

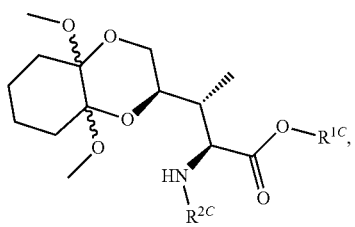

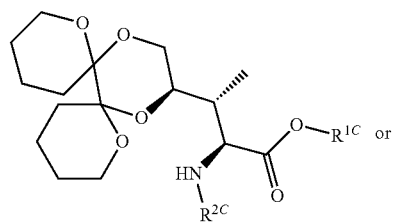 or

-continued

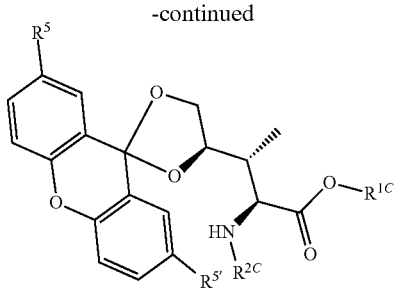

wherein $R^{1C}$ and $R^{2C}$ have the same meaning as defined above and $R^5$ and $R^{5'}$ are independently selected from H and $CH_3$.

2. The method according to claim 1, wherein
   a. $R^1$ is H or tert-butyl, and/or
   b. $R^2$ is fluorenylmethyloxycarbonyl (Fmoc) or H, and/or
   c. $R^3$ and/or $R^4$ is selected from p-methoxy benzylidene, acetonide, acetate and trialkylsilyl, and/or
   d. $R^2$ is Fmoc and $R^3$ and $R^4$ together are a benzyl or a substituted phenylmethyl, a dialkyl-substituted silyl group or a tetrasubstituted siloxane moiety.

3. The method according to claim 1, which comprises step (c).

4. The method according to claim 3, wherein the chiral ligand in step (c) is hydroquinidine 1,4-phthalazinediyl diether.

5. The method according to claim 3, wherein, subsequent to step (c), any amino group protecting moiety $R^{2C}$ and/or carboxylic acid group protecting moiety $R^{1C}$ is selectively removed from 2-amino-3-methyl-4,5-dihydroxypentanoic acid derivative (430) to yield the free (2S, 3R, 4R)-4,5-dihydroxyisoleucine.

6. The method according to claim 3, wherein, subsequent to step (c), 2-amino-3-methyl-4,5-dihydroxypentanoic acid derivative (430) is reacted with a vicinal diol protecting group.

7. The method according to claim 6, wherein 2-amino-3-methyl-4,5-dihydroxypentanoic acid derivative (430) is reacted with a vicinal diol protecting group to yield a compound selected from

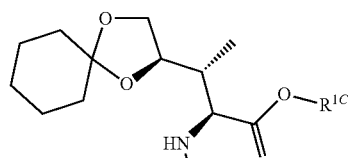

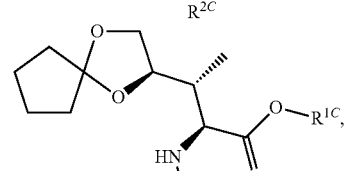

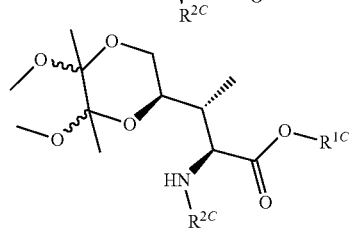

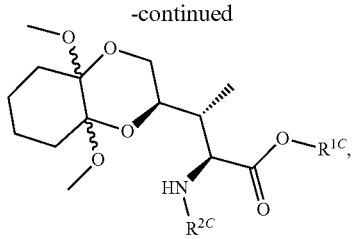

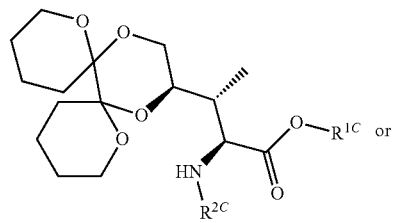

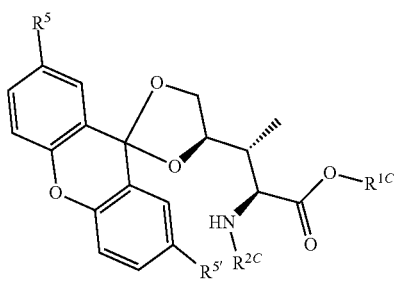

wherein $R^{1C}$ and $R^{2C}$ have the same meaning as defined above and $R^5$ and $R^{5'}$ are independently selected from H and $CH_3$.

8. The method according to claim 1, which comprises step (d).

9. The method according to claim 8, wherein, subsequent to step (d), any amino group protecting moiety $R^{2C}$ and/or carboxylic acid group protecting moiety $R^{1C}$ is selectively removed from 2-amino-3-methyl-4,5-dihydroxypentanoic acid derivative (430) to yield the free (2S, 3R, 4R)-4,5-dihydroxyisoleucine.

10. The method according to claim 8, wherein, subsequent to step (d), 2-amino-3-methyl-4,5-dihydroxypentanoic acid derivative (430) is reacted with a vicinal diol protecting group.

11. The method according to claim 10, wherein 2-amino-3-methyl-4,5-dihydroxypentanoic acid derivative (430) is reacted with a vicinal diol protecting group to yield a compound selected from

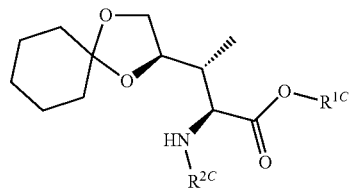

-continued
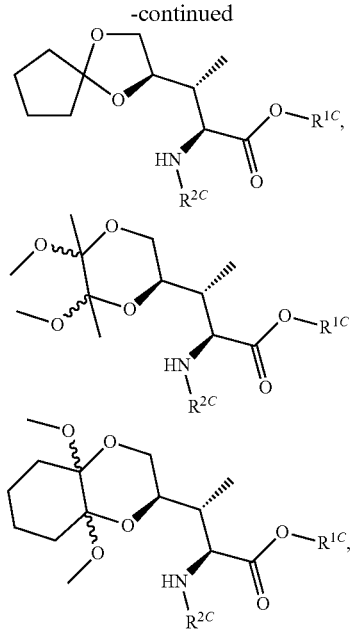
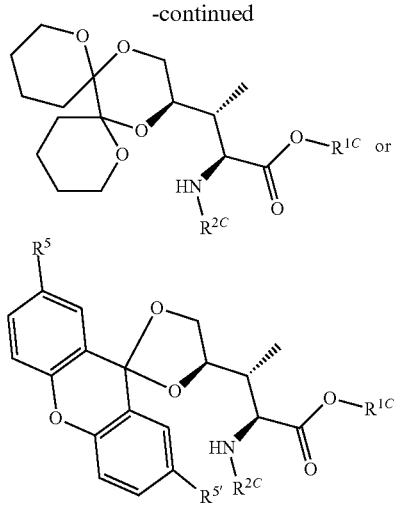
wherein $R^{1C}$ and $R^{2C}$ have the same meaning as defined above and $R^5$ and $R^{5'}$ are independently selected from H and $CH_3$.
* * * * *